(12) United States Patent
Kuwana

(10) Patent No.: US 7,262,062 B2
(45) Date of Patent: Aug. 28, 2007

(54) DIAGNOSTIC FOR SCLERODERMA

(75) Inventor: Masataka Kuwana, Tokyo (JP)

(73) Assignee: Keio University, Tokyo (JP)

( * ) Notice: Subject to any disclaimer, the term of this patent is extended or adjusted under 35 U.S.C. 154(b) by 154 days.

(21) Appl. No.: 10/877,683

(22) Filed: Jun. 25, 2004

(65) Prior Publication Data

US 2005/0042652 A1    Feb. 24, 2005

Related U.S. Application Data

(63) Continuation-in-part of application No. PCT/JP02/12909, filed on Dec. 10, 2002.

(30) Foreign Application Priority Data

Dec. 27, 2001  (JP) .............................. 2001-397811

(51) Int. Cl.
*G01N 33/564* (2006.01)
*G01N 33/53* (2006.01)
*C07K 14/435* (2006.01)
*C07K 16/18* (2006.01)
*C07K 16/42* (2006.01)

(52) U.S. Cl. .................. 436/506; 530/350; 530/387.1; 530/387.2; 530/387.9; 530/388.1; 530/358; 435/7.1

(58) Field of Classification Search .................... None
See application file for complete search history.

(56) References Cited

OTHER PUBLICATIONS

Kuwana M, Kimura K, Kawakami Y, Identification of an immunodominat epitope on RNA polymerase III recognized by systemic sclerosis sera, Oct. 2002, Arthritis Rheum 46: 2742-2747.*
Chan EKL, Tan EM, Human autoantibody-reactive epitopes of SS-B/La are highly conserved in comparison with epitopes recognized by murine monoclonal antibodies, 1987, J Exp Med 166: 1627-1640.*
Chang M, Wang RJ, Yangco DT, Sharp GC, Komatireddy GR, Hoffman RW, Analysis of autoantibodies against RNA polymerases using immunoaffinity-purified RNA polymerase, I, II, and III antigen in an enzyme-linked immunosorbant assay, 1998, Clin Immunol Immunopathol 89: 71-78.*
Rose KM, Maguire KA, Wurpel JND, Stetler DA, Marquez ED, Monoclonal antibodies directed against mammalian RNA polymerase I, 1983, J Biol Chem 258: 12976-12981.*

Masataka Kuwana, et al., Autoantibodies to RNA Polymerases Recognize Multiple Subunits And Demonstrate Cross-Reactivity With RNA Polymerase Complexes, Arthritis & Rheumatism, vol. 42, Feb. 1999, p. 275-284.
Tri Giang Phan, et al., Anti-RNA Polymerase III Antibodies In The Diagnosis Of Scleroderma Renal Crisis Sine Scleroderma, Journal of Rheumatology, 1999, 26:11, p. 2489-2492.
Setareh Sepehri, et al., The Largest Subunit Of Human RNA Polymerase III Is Closely Related To The Largest Subunit Of Yeast And Trypanosome RNA Polymerase III, Genome Research, 1997, 7, p. 1006-1019.
Gunduz OH, et al. Systemic sclerosis with renal crisis and pulmonary hypertension: a report of eleven cases. Arthritis, & Rheumatism 44: 1663-1666, 2001.
Harvey GR, et al. Clinical and serological associations with anti-RNA polymerase antibodies in systemic sclerosis. Clin Exp Immmunol 115: 395-402, 1999.
Horn HC, et al. Renal crisis in asclerodermic scleroderma-lupus overlap syndrome. Lupus 10: 886-888.
Jacobsen S, et al. Influence of clinical features, serum antinuclear antibodies, and lung function on survival of patients with systemic sclerosis. J Rheumatology 28: 2454-2459, 2001.
Chang M et al. Analysis of autoantibodies against RNA polymerases using immunoaffinity-purified RNA polymerase I, II and III antigen in an enzyme-linked immunosorbent assay. Clin Immunol Immunopathol 89: 71-78, 1998.

* cited by examiner

*Primary Examiner*—Scott D. Priebe
*Assistant Examiner*—Michael Burkhart
(74) *Attorney, Agent, or Firm*—Frommer Lawrence & Haug LLP; Thomas J. Kowalski

(57) ABSTRACT

As anti-RNA polymerase (RNAP) antibodies are detected with high frequency in patients suffering from cutaneous scleroderma where skin sclerosis progresses rapidly, supervenes scleroderma renal crisis at a high rate, and associates with clinical entities whose prognoses are extremely bad, it is intended to provide a convenient method of detecting an anti-RNAP antibodies, which is extremely useful in diagnosing and classifying clinical entities of scleroderma, and predicting organ failure, in particular scleroderma renal crisis. In order to identify an epitope recognized commonly by anti-RNAP antibodies, the full length of RPC62 and a partial fragment of RPC155, that are 2 subunits of 62-kDa and 155-kDa of RNAP III, are expressed in *Escherichia coli* as recombinant proteins, and the reactivities to sera positive and negative to anti-RNAP antibody from patients suffering from scleroderma are examined by immunoblotting method to confirm that an epitope recognized by anti-RNAP antibodies in the sera from the patients suffering from scleroderma exists in 891 to 1020 amino acid residues of RPC155.

6 Claims, 2 Drawing Sheets

DIAGNOSTIC FOR SCLERODERMA

REFERENCE TO RELATED APPLICATIONS

This application is a continuation-in-part of International Patent Application PCT/JP02/12909 filed Dec. 10, 2002 and published as WO 03/056332 filed Jul. 10, 2003 which claims priority from Japanese Patent Application Number 2001-397811 filed Dec. 27, 2001. Each of these applications, and each application and patent mentioned in this document, and each document cited or referenced in each of the above applications and patents, including during the prosecution of each of the applications and patents ("application cited documents") and any manufacturer's instructions or catalogues for any products cited or mentioned in each of the applications and patents and in any of the application cited documents, are hereby incorporated herein by reference.

Furthermore, all documents cited in this text, and all documents cited or referenced in documents cited in this text, and any manufacturer's instructions or catalogues for any products cited or mentioned in this text, are hereby incorporated herein by reference.

It is noted that in this disclosure, terms such as "comprises", "comprised", "comprising", "contains", "containing" and the like can have the meaning attributed to them in U.S. Patent law; e.g., they can mean "includes", "included", "including" and the like. Terms such as "consisting essentially of" and "consists essentially of" have the meaning attributed to them in U.S. Patent law, e.g., they allow for the inclusion of additional ingredients or steps that do not detract from the novel or basic characteristics of the invention, i.e., they exclude additional unrecited ingredients or steps that detract from novel or basic characteristics of the invention, and they exclude ingredients or steps of the prior art, such as documents in the art that are cited herein or are incorporated by reference herein, especially as it is a goal of this document to define embodiments that are patentable, e.g., novel, nonobvious, inventive, over the prior art, e.g., over documents cited herein or incorporated by reference herein. And, the terms "consists of" and "consisting of" have the meaning ascribed to them in U.S. Patent law; namely, that these terms are closed ended.

TECHNICAL FIELD

The present invention relates to a method of detecting anti-RNA polymerase antibodies (anti-RNAP antibodies), a diagnostic agent for scleroderma and a peptide for diagnosis or therapy for scleroderma, and the like.

BACKGROUND

Scleroderma (systemic sclerosis) is a type of collagen diseases which is a disease whose major symptoms are fibrosis of skin and organs of viscera such as lung, intestine and the like, and disturbances of peripheral circulation. In Japan, it is speculated that there are approximately 10,000 patients, and approximately 500 to 1,000 of new cases are developing every year. Along with the advance in medical science, improvement of the prognoses of various types of collagen diseases have been reported, but the fundamental therapeutic method for scleroderma has not been yet established, and it is a disease whose prognosis is so bad that 10-year survival rate is less than 70%. Symptoms in patients suffering from scleroderma vary and have a wide range from the patients with only extremely light disturbances of circulation who require no treatment at all to the patients who die of respiratory failure, renal failure, cardiac failure or the like within a short period. Therefore, it is extremely important to predict what kind of organ failure will progress in the future of a patient diagnosed as having scleroderma.

In the sera from the patients suffering from scleroderma, autoantibodies (antinuclear antibodies) against nuclear protein which have important biological activities such as topoisomerase I, centromere and the like, are detected with high frequency. As these autoantibodies are specific to scleroderma, they are used in its diagnosis. Further, as anti-topoisomerase I antibodies are associated with diffuse cutaneous scleroderma accompanying pulmonary fibrosis where its range of skin sclerosis is wide, while anti-centromea antibodies are associated with limited cutaneous scleroderma where visceral lesions are few and skin sclerosis is localized in fingers, detecting these antinuclear antibodies are also useful in classifying clinical entities and predicting future organ failures (Arthritis Rheum, 37:75-83, 1994). The antinuclear antibodies, which are specific to scleroderma and useful in diagnosing and classifying clinical entities, are shown in table 1, and among them whose measuring kits are released, and it is measurable in general practice, are only 3 kinds, i.e., anti-topoisomerase I antibodies, anti-centromere antibodies and anti-U1RNP antibodies.

TABLE 1

| Antinuclear antibody | Positive frequency | Range of skin sclerosis | Visceral lesion |
|---|---|---|---|
| Anti-topoisomerase I antibodies (Anti-Scl-70 antibody) | 25% | Diffuse | Pulmonary fibrosis, Skin ulcer |
| Anti-centromere antibodies | 20% | Limited | Rare cardiac, renal and pulmonary, failures, Primary biliary cirrhosis |
| Anti-U1RNP antibodies | 20% | Limited | Myositis, Pulmonary hypertension |
| Anti-RNA polymerase antibodies | 5% | Diffuse | Scleroderma renal crisis, Myocardial failure |
| Anti-U3RNP antibody | 3% | Diffuse | Few visceral failures |
| Anti-Th/To antibody | 2% | Limited | Few visceral failures |
| Anti-PM-Scl antibodies | <1% | Limited | Myositis |
| Anti-Ku antibodies | 2% | Limited | Myositis |

Anti-RNAP antibodies are antibodies found in the sera from patients suffering from scleroderma were identified as antinuclear antibodies recognizing several RNA polymerases (RNAPs) simultaneously for the first time in 1993 by the present inventors (J Clin Invest 91:1399-404, 1993). RNAP is an enzyme catalyzing the transcription of RNA, and RNAP I, RNAP II and RNAP III transcribe ribosomal RNA, messenger RNA and transfer RNA, respectively. Antibodies that simultaneously recognizing RNAP I and RNAP III were detected in the sera from patients suffering from scleroderma, and a part of which also reacts to RNAP II. Anti-RNAP antibodies have extremely high specificity to scleroderma, which has not been reported heretofore except in patients suffering from scleroderma. Anti-RNAP antibodies are detected with high frequency in diffuse cutaneous scleroderma where skin sclerosis progresses rapidly, and they supervene scleroderma renal crisis at a high rate and associate with clinical entities whose prognoses are extremely bad. Before 1980s when there was no therapeutic method for scleroderma renal crisis, the 5-year survival rate was only 30%. Many of fatal cases die of complication called scleroderma renal crisis where blood pressure rises acute, and renal failures are accompanied. Since the beginning of 1990s, a specific medicine against scleroderma renal crisis (ACE inhibitor) was found, and it was shown that administrating them in the early phase of sideration of scleroderma renal crisis allowed the patients to survive without leaving a sequela. However, although an ACE inhibitor is administered after the symptoms of scleroderma, renal crisis progress and renal function changed for the worse. Effectiveness of the ACE inhibitor is not expected. Even including fatal cases, although the patients can recover, dialysis is necessary for many of them. Therefore, the patients detected anti-RNAP antibodies related to scleroderma renal crisis recommended ensuring the self-blood pressure measurement for early detection of scleroderma renal crisis. Consequently, anti-RNAP antibodies are extremely useful antinuclear antibodies in diagnosing and classifying clinical entities of scleroderma, and predicting organ failure of scleroderma, in particular scleroderma renal crisis. Further, it is thought that examining the presence of anti-RNAP antibodies in diagnosing brings about the early detection of scleroderma renal crisis, decrease of the fatal cases by early therapy and improvement of life prognoses of scleroderma.

It has been reported by the present inventors that positive frequency of anti-RNAP antibodies in Japanese patients suffering from scleroderma is as low as about 5%, while in Caucasian patients in Europe and the United States, the rate is as high as 20-30%, whose frequency is higher than that of anti-topoisomerase I antibodies, anti-centromere antibodies and anti-U1RNP antibodies, and that anti-RNAP antibodies are the highest detected antinuclear antibodies in scleroderma in Caucasian in Europe and the United States (Arthritis Rheum 37, 902-6, 1994). Then, these results have been confirmed by the supplementary examinations in several facilities in Europe and the United States (Ann Intern Med, 119, 1005-13, 1993, Clin Exp Immunol, 105, 468-74, 1996).

Although anti-RNAP antibodies are clinically very useful antinuclear antibodies, a cumbersome immunoprecipitation which uses large amount of isotopes and cultured cells is the only method of detecting currently, therefore the present situation is that detecting anti-RNAP antibodies in a general clinical laboratory is thought to be impossible, and the detection can be performed only in specialized laboratories. Consequently, the development of a convenient method of detecting anti-RNAP antibodies is thought to be an urgent task. However, anti-RNAP antibodies cannot be detected by double immunodiffusion and immunoblotting by using crude antigens which are commonly performed for detecting antinuclear antibodies. The both of RNAP I and RNAP III are giant complexes comprising 10 or more subunits, and the number of molecules of respective subunits per cell are extremely few, can be exemplified as its reasons. In order to solve this point, identifying antigenic sites (epitopes) which are commonly recognized by anti-RNAP antibodies in the sera from patients suffering from scleroderma is essential.

Development of the method of detecting including enzyme linked immunoassay (ELISA) is thought to be possible by expressing the sites in a large amount as recombinant proteins, when epitope regions on the RNAP I and RNAP III molecules become clear. An object of the present invention is to provide a convenient method of detecting anti-RNAP antibodies, which is extremely useful in diagnosing and classifying clinical entities of scleroderma, and predicting organ failure, in particular scleroderma renal crisis, and which has extremely high specificity to scleroderma, as they are detected with high frequency in the patients suffering from diffuse cutaneous scleroderma where skin sclerosis progresses rapidly, and they supervene scleroderma renal crisis at a high rate and related to clinical entities whose prognoses are extremely bad.

A basic study by the present inventors resulted in the elucidation that anti-RNAP antibodies in the sera from patients suffering from scleroderma recognize 2 subunits of 155-kDa and 62-kDa (RPC155, RPC62) of RNAP III with high frequency (Arthritis Rheum, 42, 275-84, 1999). In addition, cDNA sequence of human RPC155 was reported by Setareh and Hernandez in 1997 (Genome Res, 7, 1006-19, 1997), and it is registered to database of NCBI (accession No. AF021351). Then, in order to identify the epitopes existing on RPC155 and RPC62 in more detail, the full-length protein of RPC62 and a partial fragment of RPC155 were expressed as recombinant proteins in *Escherichia coli* and the reactivities to sera positive and negative to the anti-RNAP antibody from patients suffering from scleroderma were examined by immunoblotting. First, study using the recombinant proteins of RPC155-A (Seq. ID No. 8), RPC155-B2 (Seq. ID No. 10), RPC155-C (Seq. ID No. 12), RPC155-D (Seq. ID No.14) and RPC62 (full-length) shown in FIG. 1, led to the result shown in Table. 2. Each recombinant protein was recognized by sera positive to anti-RNAP antibody, while all of 11 sera positive to anti-RNAP antibodies reacted to RPC155-C.

TABLE 2

| Recombinant RNAP III Fragment | Scleroderma Anti-RNAP Antibody(+) (n = 11) | Scleroderma Anti-RNAP Antibody(−) (n = 10) | Normal Person (n = 6) |
| --- | --- | --- | --- |
| RPC155-A | 2(18%) | 1(10%) | 0 |
| RPC155-B2 | 1(9%) | 0 | 0 |
| RPC155-C | 11(100%) | 0 | 0 |
| RPC155-D | 3(27%) | 0 | 0 |
| RPC62 | 6(55%) | 0 | 0 |

There, in order to examine epitopes contained in RPC155-C in more detail, 5 recombinant fragments of C1-C5 shortened from N- and C-terminals of RPC155-C were newly generated. When the reactivities to 11 sera that were positive to anti-RNAP antibodies were studied by immunoblotting, all of the sera recognized C3 and C4, while they did not react to C1, C2 and C5. Further, 7 recombinants of C-a to C-g encoding the common site of C3 and C4 were generated to examine the reactivities to sera positive to anti-RNAP antibody similarly. All of the sera reacted to C-c and C-g, while they did not recognize other recombinant fragments. Consequently, it was revealed that there are epitopes recognized commonly by anti-RNAP antibodies in the sera from patients suffering from scleroderma, at No. 891-1020 amino acid residues of RPC155 encoded by C-c. However, as the reactivity to C-c was weaker than that to C-g in certain sera, it was predicted that an amino acid site contained additionally in C-g was also necessary for strong binding to antibodies in the sera from patients. Therefore, it was revealed that C-g is more suitable than C-c for detecting anti-RNAP antibodies.

In order to confirm that the reactivity to C-g is specific to anti-RNAP antibodies in the sera from patients suffering from scleroderma, the study by immunoblotting with more examples was performed. As a result, the reactivity to C-g was detected in all of the 16 positive cases of scleroderma to anti-RNAP antibody, while it was not detected in 55 negative cases to anti-RNAP antibody scleroderma and 26 cases of normal person. Consequently, it was thought that C-g comprises epitopes recognized commonly by anti-RNAP antibodies in the sera from patients suffering from scleroderma, and recombinant proteins expressing the same sites are useful as antigens in methods of detecting anti-RNAP antibodies. Then, after C-g was expressed in Escherichia coli, it was purified by affinity column, and used as an antigen for ELISA. As shown in FIG. 2, reactivity to C-g in sera negative to anti-RNAP antibody scleroderma, the sera from patients suffering from systemic lupus erythematosus and sera from normal person used as controls tested by conventional immunoprecipitation were at a low level. When 4.15 units represented by the average of data+5× standard deviation from normal person was made to be cutoff, positive frequency of anti-C-g antibodies showed 100% in examples positive to anti-RNAP antibody and showed 0% in other examples, which revealed that ELISA by using C-g is an extremely superior method of detecting anti-RNAP antibodies where both sensitivity and specificity were 100%. The present invention has been completed based on these knowledges.

DISCLOSURE OF THE INVENTION

The present invention relates to a method of detecting an anti-RNA polymerase antibody, wherein the following peptides are used: (a) a peptide consisting of an amino acid sequence shown by Seq. ID No. 2, (b) a peptide comprising the whole of the amino acid sequence shown by Seq. ID No. 2, preferably a peptide consisting of an amino acid sequence shown by Seq. ID No. 4, (c) a peptide comprising an amino acid sequence including a part of an amino acid sequence shown by Seq. ID No. 2, and having an antinuclear antibody-binding capacity, (d) a peptide comprising an amino acid sequence where one or more amino acids are deleted, replaced or added in an amino acid sequence shown by Seq. ID No. 2, and having an antinuclear antibody-binding capacity (e) a peptide comprising an amino acid sequence including the whole of the amino acid sequence where one or more amino acids are deleted, replaced or added in an amino acid sequence shown by Seq. ID No. 4, and having an antinuclear antibody-binding capacity, preferably a peptide comprising an amino acid sequence including the whole of the amino acid sequence where one or more amino acids are deleted, replaced or added in an amino acid sequence shown by Seq. ID No. 4, and having an antinuclear antibody-binding capacity, and (f) a peptide comprising an amino acid sequence including a part of an amino acid sequence where one or more amino acids are deleted, replaced or added in an amino acid sequence shown by Seq. ID No. 2, and having an antinuclear antibody-binding capacity ("1"); the method of detecting an anti-RNA polymerase antibody according to "1", wherein the peptide is a peptide consisting of an amino acid sequence shown by Seq. ID No. 4, or a peptide comprising an amino acid sequence including the whole of the amino acid sequence where one or more amino acids are deleted, replaced or added in an amino acid sequence shown by Seq. ID No. 4, and having an antinuclear antibody-binding capacity ("2"); a diagnostic agent comprising the following peptides: (a) a peptide consisting of an amino acid sequence shown by Seq. ID No. 2, (b) a peptide comprising the whole of the amino acid sequence shown by Seq. ID No. 2, (c) a peptide comprising an amino acid sequence including a part of an amino acid sequence shown by Seq. ID No. 2, and having an antinuclear antibody-binding capacity (d) a peptide comprising an amino acid sequence where one or more amino acids are deleted, replaced or added in an amino acid sequence shown by Seq. ID No. 2, and having an antinuclear antibody-binding capacity, (e) a peptide comprising an amino acid sequence including the whole of the amino acid sequence where one or more amino acids are deleted, replaced or added in an amino acid sequence shown by Seq. ID No. 2, and having an antinuclear antibody-binding capacity, and (f) a peptide comprising an amino acid sequence including a part of an amino acid sequence where one or more amino acids are deleted, replaced or added in an amino acid sequence shown by Seq. ID No. 2, and having an antinuclear antibody-binding capacity ("3"); the diagnostic agent according to "3", wherein the peptide is a peptide consisting of an amino acid sequence shown by Seq. ID No. 4, or a peptide where one or more amino acids are deleted, replaced or added in an amino acid sequence shown by Seq. ID No. 4, and having an antinuclear antibody-binding capacity ("4"); a diagnostic or therapeutic peptide for scleroderma comprising the following peptides: (a) a peptide consisting of an amino acid sequence shown by Seq. ID No. 2, (b) a peptide comprising the whole of the amino acid sequence shown by Seq. ID No. 2, (c) a peptide comprising an amino acid sequence including a part of an amino acid sequence shown by Seq. ID No. 2, and having an antinuclear antibody-binding capacity, (d) a peptide comprising an amino acid sequence where one or more amino acids are deleted, replaced or added in an amino acid sequence shown by Seq. ID No. 2, and having an antinuclear antibody-binding capacity, (e) a peptide comprising an amino acid sequence including the whole of the amino acid sequence where one or more amino acids are deleted, replaced or added in an amino acid sequence shown by Seq. ID No. 2, and having an antinuclear antibody-binding capacity, and (f) a peptide comprising an amino acid sequence including a part of an amino acid sequence where one or more amino acids are deleted, replaced or added in an amino acid sequence shown by Seq. ID No. 2, and having an antinuclear antibody-binding capacity ("5"); the diagnostic or therapeutic peptide for scleroderma according to "5", wherein the peptide is a peptide consisting of an amino acid sequence shown by Seq. ID No. 4, or a peptide comprising an amino acid sequence including the whole of the amino acid where one or more amino acids are deleted, replaced or added in an amino acid sequence shown by Seq. ID No. 4, and having an antinuclear antibody-binding capacity ("6"); a monoclonal antibody recognizing the following peptides: (a) a peptide consisting of an amino acid sequence shown by Seq. ID No. 2, (b) a peptide comprising the whole of the amino acid sequence shown by Seq. ID No. 2, (c) a peptide comprising an amino acid sequence including a part of an amino acid sequence shown by Seq. ID No. 2, and having an antinuclear antibody-binding capacity, (d) a peptide comprising an amino acid sequence where one or more amino acids are deleted, replaced or added in an amino acid sequence shown by Seq. ID No. 2, and having an antinuclear antibody-binding capacity (e) a peptide comprising an amino acid sequence including the whole of the amino acid sequence where one or more amino acids are deleted, replaced or added in an amino acid sequence shown by Seq. ID No. 2, and having an antinuclear antibody-binding capacity, and (f) a peptide comprising an amino acid sequence including a part of an amino acid sequence where one or more amino acids are deleted, replaced or added in an amino acid sequence shown by Seq. ID No. 2, and having an antinuclear antibody-binding capacity ("7"); the monoclonal antibody according to "7", wherein the peptide is a peptide consisting of an amino acid sequence shown by Seq. ID No. 4, or a peptide comprising an amino acid sequence including the whole of the amino acid sequence where one or more amino acids are deleted, replaced or added in an amino acid sequence shown by Seq. ID No. 4, and having an antinuclear antibody-binding capacity ("8"); an anti-idiotypic antibody against the monoclonal antibody according to "7" or "8" ("9"); and the anti-idiotypic antibody according to "9", that is diagnosis or therapy for scleroderma ("10").

DETAILED DESCRIPTION

Figure 1:
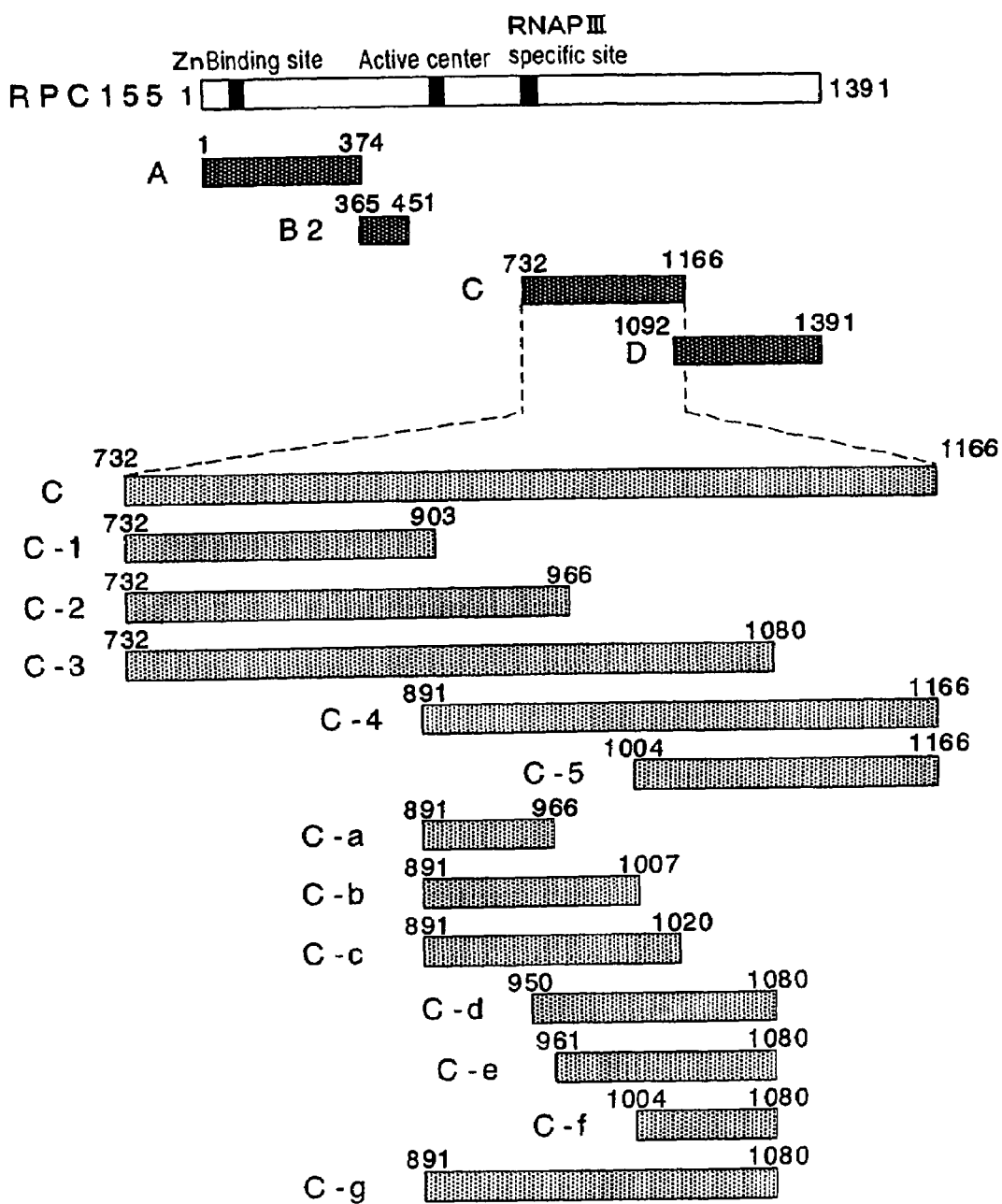
FIG. 1 is a figure showing recombinant fragments of RPC155, used for analysis of epitope region of RNAP subunits recognized commonly by anti-RNAP antibodies in the sera from patients suffering from scleroderma.

As for the present peptides used in the method of detecting the anti-RNAP antibodies of the present invention, and used for producing diagnostic agents for scleroderma, diagnostic or therapeutic peptide for scleroderma, monoclonal antibodies, anti-idiotypic antibodies which are diagnostic or therapeutic for scleroderma of the present invention, peptides that are translated products of subunit gene (accession No. NM-007055) of DNA-dependent RNAP III existing on No. 10 human chromosome (10q22-q23), and that are represented by No. [AA] 891-1020 of the amino acid residues (Seq. ID No.2) which is a partial amino acid sequence of subunit RPC155 of 155-kDa consisting of an amino acid sequence shown by Seq. ID No. 6, preferably peptides represented by No. AA 891-1080 (Seq. ID No. 4), are suitably exemplified.

Further, as for the present peptides, peptides comprising the whole of the amino acid sequence shown by Seq. ID No. 2 or 4, for instance, peptides represented by No. AA732-1166 of RPC155 (Seq. ID No. 12), No. AA732-1080 of RPC155 and No. AA891-1166 of RPC155, and peptides comprising an amino acid sequence including a part of an amino acid sequence shown by Seq. ID No. 2 or 4, and having an antinuclear antibody-binding capacity, can be exemplified. Here, the peptides having antinuclear antibody-binding capacities are peptides that can bind to anti-RNAP antibodies of peptides and the like comprising the epitopes recognized by anti-RNAP antibodies.

Besides, as for the present peptides, peptides comprising an amino acid sequence shown by Seq. ID No. 2 or 4, or comprising an amino acid sequence where one or more amino acids are deleted, replaced or added in an amino acid sequence containing whole or part of the amino acid sequence shown by Seq. ID No. 2 or 4, and having an antinuclear antibody-binding capacity can be exemplified.

Specifically, peptides where glycin at No. AA 1056 in an amino acid sequence shown by Seq. ID No. 4 is replaced with alanine, can be exemplified.

The method of preparing the present peptides is not particularly restricted, but a method of preparing the peptides as recombinant peptides (recombinant fragments) by the conventional method based on the base sequence information of DNA encoding the present peptides, can be preferably exemplified. When prokaryotic cells, etc. are made to be host cells, they may be expressed as fusion proteins. Further, the present peptides can also be prepared by purifying from cultured cells and tissues. Meantime, as epitope region of human RPC155 has high homology with RPC155 of other nucleated organisms, and derivation of RPC155 is not restricted to human.

As for the method of detecting anti-RNAP antibodies of the present invention, it is not particularly restricted as long as it is a method of detecting anti-RNAP antibodies by using the present peptides, enzyme linked immunoassay (ELISA), fluorescence immunoassay, immunoblotting, dot blotting, immunodiffusion method and the like can be specifically exemplified, and heterogeneous ELISA is preferable among them. As for the ELISA, double antibody sandwich assay where enzyme-labeled antibodies against anti-RNAP antibodies recognizing the solid phased present peptides, direct antibody method where the labeled present peptides bound to the solid phase are contacted anti-RNAP antibodies in the samples, indirect antibody method, competition method and the like can be exemplified. As for the solid phase, microtiter well, agarose, latex particles, magnetic microparticles and the like can be exemplified, and as for the labeled enzyme, horseradish peroxidase, alkaline phosphatase, galactosidase and the like can be exemplified. In the meantime, methods of detecting and analyzing anti-RNAP antibodies are included in the method of detecting anti-RNAP antibodies of the present invention.

As for the samples to be the objects of the method of detecting anti-RNAP antibodies of the present invention, it is not particularly restricted, but humor such as serum, plasma, saliva, cerebrospinal fluid, urine, and the like can be exemplified generally, and the sera from the patients suffering from scleroderma such as diffuse cutaneous scleroderma positive to anti-RNAP antibody can be preferably exemplified. When recombinant peptides are used, it is preferable to react components of host-cell such as components of *Escherichia coli* to samples such as sera in advance, to remove the antibodies which react to components of host-cell such as components of *Escherichia coli*. When recombinant fusion peptides are used, it is preferable to react components of host-cell and fusion components to the samples such as sera in advance, to remove the antibodies which react to components of the host-cell and fusion components.

As for the diagnostic agent of the present invention, it is not particularly restricted as long as it is a diagnostic agent for scleroderma comprising the present peptides, with which the method of detecting the anti-RNAP antibodies of the aforementioned present invention can be performed, for instance, a diagnostic kit for scleroderma including solid phased present peptides, ELISA buffer for diluting serum, enzyme-labeled secondary antibodies, an enzyme substrate, components of host-cell and the like, can be preferably exemplified. The diagnostic agent of the present invention is useful in diagnosing and classifying clinical entities of scleroderma, and predicting organ failure.

As for the peptide for diagnosis or therapy for scleroderma of the present invention, it is not particularly restricted as long as it is the peptide comprising the present peptide, as for the diagnostic peptide for scleroderma, fusion protein or fusion peptide which are prepared by binding the present peptide to marker protein/or peptide tag as well as the solid phased present peptide, can be exemplified. As for the aforementioned marker protein, conventionally known marker proteins, such as alkaline phosphatase, Fc region of antibodies, HRP, GFP and the like can be specifically exemplified. Further, as for the peptide tag, conventionally known peptide tags, such as His tag, FLAG tag, S tag and the like can be specifically exemplified. The fusion proteins and fusion peptides can be prepared by the conventional method, and they are also useful in quantifying anti-RNAP antibodies, and as diagnostic markers for scleroderma and the like, as well as a laboratory reagent in the field of interest.

Therapeutic peptide for scleroderma of the present invention can also be administered as a recombinant vector introduced DNA encoding the present peptide. As for the recombinant vector, a recombinant vector comprising expression system which can express the present peptides in the host cells is preferable, for instance, the expression system derived from chromosome, episome and virus, and more specifically a vector such as derived from bacterial plasmid, derived from yeast plasmid, derived from papovavirus such as SV40, vaccinia virus, adenovirus, fowlpox virus, pseudorabies virus, and retrovirus, and a vector derived from bacteriophage, derived from transposon, and derived from their combination, for instance, a vector derived from genetic element of plasmid and bacteriophage such as cosmids and phagemids, can be exemplified. This expression system may contain a regulatory sequence that not only causes the expression but also regulates the expression. Moreover, as for the aforementioned method of administrating the therapeutic peptide for scleroderma of the present invention, either oral administration or parental administration such as intravenous injection is suitable, and dosage can be suitably decided in consideration for method of administering, symptoms/age of the patient, physical property of anti-inflammatory substance and the like. Further, as for dosage forms, tablets, capsules, granules, powder, syrup, suspension, suppository, ointment, cream, gel, adhesive preparation, respiratory tonic, injectable solutions and the like can be specifically exemplified, and these preparations are generally administered in the form of preparations prepared by mixing with carriers for preparation.

As for the monoclonal antibodies of the present invention, it is not particularly restricted as long as it is a monoclonal antibody recognizing the present peptides, and the monoclonal antibodies can be prepared by the conventional method by using the aforementioned present peptides. That is, any method such as a hybridoma method (Nature 256, 495-497, 1975), trioma method, human B cell hybridoma method (Immunology Today 4, 72, 1983) and EBV-hybridoma method (MONOCLONAL ANTIBODIES AND CANCER THERAPY, pp. 77-96, Alan R. Liss, Inc., 1985) that the antibodies were prepared by administrating these fragments including the present peptides or epitopes to animals (preferably non-humans) and cause the antibodies generated by cultures, such as a continuous cell system, can be used. The monoclonal antibodies are useful as a standard in the method of detecting the anti-RNAP antibodies of the present invention including ELISA, and in a diagnostic agent for scleroderma of the present invention, further in affinity purifying the present peptide, and in others such as in revealing the onset mechanism of scleroderma.

As for the anti-indiotype antibodies of the present invention, it is not particularly restricted as long as it is an antibody against the monoclonal antibody recognizing the present peptide, and the anti-indiotype antibody can be generated by the conventional method by using the aforementioned monoclonal antibodies of the present invention and the fragments comprising their variable regions with hybridoma method and the like. Moreover, the anti-indiotype antibodies of the present invention can be used for diagnosis and therapy for scleroderma.

EXAMPLES

The present invention will be explained more specifically with examples below, but the technical scope of the invention is not restricted to these examples.

Example 1 [Method]

Example 1A (Preparation of Sera Positive to Anti-RNAP Antibody)

Anti-RNA polymerase (RNAP) antibodies in the sera were detected by immunoprecipitation. Soluble cell extract from Hela cells labeled with $^{35}$S-methionine (TRAN $^{35}$S-LABEL; ICN Biomedicals, Irvine, Calif., USA) used as antigens, were reacted to IgG in test sera bound to protein A Sepharose, and the sera where all of the high molecular subunits of RNAP I (190-kDa protein and 126-kDa protein) and high molecular subunits of RNAP III (155-kDa protein and 138-kDa protein) were precipitated, were considered as positive to anti-RNAP antibody. As for the test sera, the sera from 105 cases of the patients suffering from scleroderma were made to be objects, among which the sera from 16 cases were turned out to be positive to anti-RNAP antibody by immunoprecipitation. The sera from 61 cases of the patients suffering from systemic lupus erythematousus (SLE), and the sera from 61 cases of normal person were used as controls. All the cases of the patients suffering from scleroderma and SLE met the preliminary standards for classification by American College of Rheumatology.

Example 1B (Amplification of cDNA Encoding RPC62 and RPC155)

cDNA encoding the subunit of 62-kDa of RNAP III (RPC62) and cDNA encoding 4 fragments (RPC155-A, RPC155-B2, RPC155-C and RPC155-D) of subunit of 155-kDa of RNAP III (RPC155) shown in FIG. 1, were amplified by RT-PCR method, to determine the respective base sequences (RPC155-A (Seq. ID No. 7), RPC155-B2 (Seq. ID No. 9), RPC155-C (Seq. ID No. 11), RPC155-D (Seq. ID No. 12)). First, the specific primer synthesized from base sequences of cDNA of RPC62 and RPC155 registered to Genebank (Accession No. U93867 and NM-007055) was used, and ExTaq (Takara Shuzo Co. LTD, Tokyo) was used for a reactive enzyme. Condition for reaction was as follows: the cycle, where degeneration was performed for 5 min at 94° C. by using thermal cycler (Perkin-Elmer) only for the first time, then thermal denaturation was performed for 1 min at 94° C., annealing was performed for 1 min at 55° C., and extension reaction was performed for 2 min at 72° C., was repeated 35 times and extension was performed for 7 min at 72° C. at last. The obtained PCR products were DNA sequenced by using Big Dye DNA Sequencing Kit (ABI) and ABI Prism 310 genetic analyzer (Applied Biosystems, FosterCity, Calif.), to determine the respective base sequences.

Messenger RNA of poly A+ was separated from human leukemia K562 cell line by using the magnetic beads binding oligo $(dt)_{25}$ (Takara Shuzo Co. LTD, Tokyo). The mRNA was transformed into a single strand cDNA by reverse transcriptase of AMV by using oligo (dt), and further cDNA encoding all of the open reading frames (ORFs) of RPC62 was amplified, by PCR with a primer for PCR62 (sense primer: Seq. ID No. 15, antisense primer: Seq. ID No. 16) by using aforementioned single strand DNA as a template. Moreover, as for RPC155, 4 fragments ([AA] No. 1-374 of RPC155-A (Seq. ID No. 8); AA365-751 of RPC155-B; AA732-1166 of RPC155-C (Seq. ID No. 12); and AA1092-1391 of RPC155-D (Seq. ID No. 14), encoding all of the ORF redundantly were amplified by PCR by using primers for RPC155-A (sense primer; Seq. ID No. 17, antisense primer; Seq. ID No. 18), primers for RPC155-B (sense primer; Seq. ID No. 19, antisense primer; Seq. ID No. 20), primers for RPC155-C (sense primer; Seq. ID No. 21, antisense primer; Seq. ID No. 22), and primers for RPC155-D (sense primer; Seq. ID No. 23, antisense primer; Seq. ID No. 24), respectively, and by using a single strand DNA obtained from the reverse transcription reaction with random hexamer (GIBCO, Grand Island, N.Y., USA) from mRNA of K562 as a template. The obtained PCR products were subcloned to pGEM-T vector (Promega, Madison, Wis., USA). The base sequence for insert was determined by ABI Prism 310 genetic analyzer by using the primers of T7 and SP6.

Further, 12 kinds of partial fragments of C-1 to C-5, and C-a to C-g of RPC155-C shown in FIG. 1 were amplified by PCR which templated pGEM-T encoding aforementioned RPC155-C. C-1 (sense primer: Seq. ID No. 25, antisense primer: Seq. ID No. 26), C-2 (sense primer: Seq. ID No. 27, antisense primer: Seq. ID No. 28), C-3 (sense primer: Seq. ID No. 29, antisense primer: Seq. ID No. 30), C-4 (sense primer: Seq. ID No. 31, antisense primer: Seq. ID No. 32), C-5 (sense primer: Seq. ID No. 33, antisense primer: Seq. ID No. 34), C-a (sense primer: Seq. ID No. 35, antisense primer: Seq. ID No. 36), C-b (sense primer: Seq. ID No. 37, antisense primer: Seq. ID No. 38), C-c (sense primer: Seq. ID No. 39, antisense primer: Seq. ID No. 40), C-d (sense primer: Seq. ID No. 41, antisense primer: Seq. D No. 42), C-e (sense primer: Seq. ID No. 43, antisense primer: Seq. ID No. 44), C-f (sense primer: Seq. ID No. 45, antisense primer: Seq. ID No. 46), C-g (sense primer: Seq. ID No. 47, antisense primer: Seq. ID No. 48), were used as primers, respectively. Restriction enzyme sites (EcoRI site in upstream, and XbaI site in downstream) are added to all primers used in PCR of these 12 kinds of respective partial fragments of RPC155-C, in consideration for subcloning.

Example 1C (Expression of Recombinant Proteins of RPC62 and RPC155)

cDNA encoding the full length of RPC62 and a part of RPC155 prepared in Example 1B was subcloned by adjusting the frame to the downstream of MalE gene of the protein expressing vector pMAL-c2 (New England Biolabs, Beverly, Mass., USA). By adding 0.3 mM of IPTG, recombinant proteins of RNAP subunit were expressed as fusion proteins with maltose-binding protein (MBP). The recombinant proteins expressed in Escherichia coli were purified by using amylose resin in certain experiments.

Example 1D (Immunoblotting)

Escherichia coli expressing recombinant fragments of the full length of RPC62 and RPC155 were fractionated by 10% polyacrylamid-SDS gel electrophoresis, and transcribed onto nitrocellulose membrane electrically. The sera were diluted by 250 times, and reacted to component of Escherichia coli which induced the expression of MBP to remove the antibodies reacting to component of Escherichia coli and MBP in advance. Nitrocellulose membrane was reacted to the sera, and alkaline phosphatase-binding goat anti-human IgG antibodies (ICN/Cappel, Aurora, Ohio, USA), sequentially. Antibodies binding to recombinant protein were detected by coloring reaction by using NBT/BCIP as a substrate.

Example 1E (ELISA)

Purified recombinant proteins (0.5 µg/ml) diluted with 2-mercaptoethanol (0.05%) added phosphate buffered saline (PBS) were added to respective wells of 96 well polyvinyl plates (Sumilon H Plate; Sumitomo Bakelite Co., Tokyo), and left quietly at 4° C. for 12 h to be solid phased. Respective wells were added 3% bovin serum albumin (BSA) after washed once with PBS, and blocked. The sera from the patients were added to the respective wells after being diluted with ELISA buffer (0.1% BSA, 0.1% Tween 20 added PBS) by 250 times, and being removed the antibodies reacting to component of Escherichia coli and MBP by reacting them to component of Escherichia coli inducing the expression of MBP. After being reacted at the room temperature for 2 h, the wells were washed with ELISA buffer 3 times. Further, they were reacted to peroxidase binding goat anti-human IgG antibodies diluted by 5000 times at the room temperature for 1 h and washed with ELISA buffer for 3 times. Tetramethyl Benzidine dissolved to the concentration of 1 mg/ml with DMSO was mixed to phosphate/citrate buffer at a ratio of 1 to 9, and added to the respective wells as substrates. After 10 min of reaction, the wells were added 1 N of sulfuric acid to terminate the reaction. The absorbance of the respective wells at 405 nm was measured by Plate Reader (Bio-rad Laboratories, Hercules, Calif.). All of the samples were measured by 2 wells, and the mean value was calculated. The standard curve was made from dilution system of MY sera positive to anti-RNAP antibody at a high titer, and absorbance of the respective samples were converted to unit with the amount of anti-RNAP antibodies in the sera diluted by 4000 times being one unit. 4.15 units which was the mean value+3× standard deviation of sera from normal person, were made to be cut off.

Example 2 [Result]

Example 2A (Amplification of cDNA Encoding RPC62 and RPC155)

cDNA encoding the all ORFs of RPC62 could be obtained by normal RT-PCR method, but cDNA corresponding to ORF of RPC155 (Seq. ID No. 5) was so big as 4.2 kb that the amplification in its full length was a difficult task. Then, the all ORFs of RPC155 was amplificated as 4 fragments of cDNA overlapping for over 30 bp. That is, RPC 155 consisting of 1391 amino acids was amplificated as 4 cDNA fragments encoding AA1-374 (RPC155-A), AA365-751 (RPC155-B), AA732-1166 (RPC155-C) and AA1092-1391 (RPC155-D), respectively. The obtained cDNA fragments were determined their base sequences after being subcloned to pGEM-T, and they were compared to known base sequence of RPC155 (GeneBank Accession No.: NM-007055). Each fragment had a high homology, but 4 replacements of base sequence were found in RPC155-A and C, respectively, and 4 of which were accompanied with replacement of amino acids (No.15 threonine, No. 262 phenylalanine, No. 283 leucine, and No. 1056 glycine were replaced with isoleuicine, isoleuicine, proline, and alanine, respectively.) Further, No. 1276 valine comprised in RPC155-D was deleted. As these sequences were detected from several DNAs derived from colonies, and further the identical sequences were found in gene arrangements registered to GeneBank, most of them were thought to be single nucleotide polymorphisms (SNPs) existing in RPC155 gene.

Example 2B (Expression of Recombinant Proteins of RPC62 and RPC155)

Next, RPC62, RPC155-A, RPC155-B, RPC155-C, and RPC155-D were subcloned to pMAL-c2, respectively, and they were expressed as fusion proteins with MBP. In RPC155-A, RPC155-C, RPC155-D, the expressions of fusion proteins encoding respective sites were confirmed according to the base sequences of insert and molecular weight of the fusion proteins. However, a lot of clones comprising different base sequences were detected from the colonies of *Escherichia coli* introduced cDNA of RPC155-B. Deletion, insertion and mutation of bases were observed in each of the base sequences, and the clones expressing the full length of RPC155-B was not found due to framshifts and mutations to stop codons. Accordingly, the clone expressing the original amino acid sequence in the longest stretch was named RPC155-B2 (AA365-451) (Seq. ID No. 10) to use for the following analysis (FIG. 1). AA509-519 of RPC155 is conserved broadly beyond species from *Escherichia coli* to human, and thought to be the center of transcription activity. Therefore, It was highly possible that the expression of recombinant proteins including this active center worked toxically against *Escherichia coli*, and the clones having mutation in these genes were chosen.

Example 2C (Reactivities to RPC62 and RPC155 Recombinant Proteins)

The reactivities of the sera from 11 positive cases to anti-RNAP antibody scleroderma, 10 negative cases to anti-RNAP antibody scleroderma, and 6 cases of normal person to 5 recombinant proteins (RPC62, RPC155-A, RPC155-B2, RPC155-C, and RPC155-D) encoding RPC62 and RPC155, were examined by immunoblotting. As shown in aforementioned Table. 2, RPC62, RPC155-A, RPC155-B2, RPC155-C, and RPC155-D were recognized by sera positive to anti-RNAP antibody in 6 cases (55%), 2 cases (18%), 1 case (9%), 11 cases (100%) and 3 cases (27%), respectively, and there were several epitopes which react to autoantibodies on the molecules of RPC62 and RPC155. Especially, RPC155-C was recognized in all the positive cases of anti-RNAP antibodies, while it was not recognized in the sera of anti-RNAP antibody negative scleroderma and normal person. Consequently, the possibility was thought that the epitopes recognized commonly by sera positive to anti-RNAP antibodies might exist in RPC155-C.

Example 2D (Identification of Major Epitope Region on RPC155)

In order to examine the epitope region contained in RPC155-C in more detail, 5 recombinant fragments of C1-C5 shortened from N- and C-terminals of RPC 155-C were newly generated by PCR method (see FIG. 1). When the reactivity to 11 sera positive to anti-RNAP antibody was examined by immunoblotting, it was revealed that all of the sera recognized C3 and C4, but they did not react to C1, C2 and C5. Further, 7 recombinant fragments of C-a to C-g encoding the common site of C3 and C4 were generated based on the sequence information such as C-c consisting of the base sequence shown by Seq. ID No. 1 and C-g consisting of the base sequence shown by Seq. ID No.3 (see FIG. 1), and the reactivity to 11 sera positive to anti-RNAP antibody was examined similarly. All of the sera that are positive to anti-RNAP antibodies reacted to C-c and C-g, while they did not recognize other recombinant fragments. Therefore, it was revealed that there were epitopes recognized commonly by anti-RNAP antibodies in the sera from the patients suffering from scleroderma in AA891-1020 of RPC155, which is encoded by C-c. However, as the reactivity to C-c was much weaker than that to C-g in certain sera, it was predicted that amino acid section contained excessively in C-g was necessary for strong binding to antibodies in the sera from patients. In order to confirm that the reactivity to C-g was specific to anti-RNAP antibodies in the sera from patients suffering from scleroderma, examination by immunoblotting by using multiple cases was performed. As a result, the reactivities to C-g were detected in all of 16 cases of positive to anti-RNAP antibody scleroderma, while they were not detected in 55 cases of anti-RNAP antibody negative scleroderma and 26 cases of normal person.

Example 2E (Establishment of ELISA Method for Detecting Anti-RNAP Antibodies)

Figure 2:
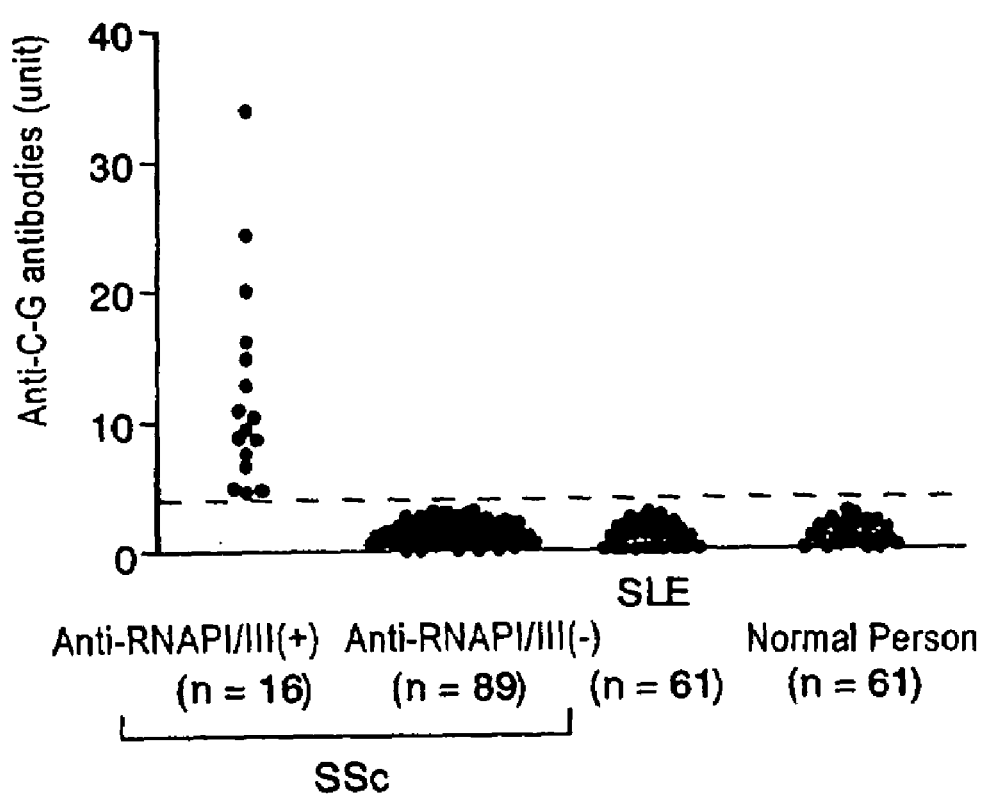
FIG. 2 is a figure showing a graph indicating the result of detection of anti-RNAP antibodies by ELISA with a recombinant fragment C-g.

Though both of C-c and C-g comprised epitopes recognized commonly by anti-RNAP antibodies, the reactivity to C-c was much weaker than that to C-g in certain sera, thus C-g was judged to be more suitable for detecting anti-RNAP antibodies than C-c. Then, C-g was purified with affinity column after being expressed in *Escherichia coli*, and it was used as an antigen for ELISA. As shown in FIG. 2, all of the sera positive to anti-RNAP antibodies showed anti-C-g antibody at high levels, while the reactivities to C-g in sera from scleroderma of anti-RNAP antibodies negative, and the sera from SLE patients and sera from normal person used as a control were at low levels as examined by the conventional immunoprecipitation. When 4.15 units which represents mean value+5×standard deviation of normal person was made to be cutoff, the positive frequency of anti-C-g antibodies became 100% in the positive cases to anti-RNAP antibody and 0% in other cases, therefore it was revealed that ELISA using C-g was an extremely effective method of detecting anti-RNAP antibodies, where both sensitivity and specificity showed 1000%.

The invention will now be further described by the following numbered paragraphs:

1. A method of detecting an anti-RNA polymerase antibody, wherein the following peptides are used:

(a) A peptide consisting of an amino acid sequence shown by Seq. ID No. 2, (b) A peptide comprising the whole of the amino acid sequence shown by Seq. ID No. 2, preferably a peptide consisting of an amino acid sequence shown by Seq. ID No. 4, (c) A peptide comprising an amino acid sequence including a part of an amino acid sequence shown by Seq. ID No. 2, and having an antinuclear antibody-binding capacity, (d) A peptide comprising an amino acid sequence where one or more amino acids are deleted, replaced or added and having an antinuclear antibody-binding capacity in an amino acid sequence shown by Seq. ID No. 2, (e) A peptide comprising an amino acid sequence including the whole of the amino acid sequence where one or more amino acids are deleted, replaced or added in an amino acid sequence shown by Seq. ID No. 2, and having an antinuclear antibody-binding capacity, and (f) A peptide comprising an amino acid sequence including a part of an amino acid sequence where one or more amino acids are deleted, replaced or added in an amino acid sequence shown by Seq. ID No. 2, and having an antinuclear antibody-binding capacity 2. The method of detecting an anti-RNA polymerase antibody according to paragraph 1, wherein the peptide is a peptide consisting of an amino acid sequence including the whole of the amino acid sequence where one or more amino acids are deleted, replaced or added in an amino acid sequence shown by Seq. ID No. 4, and having an antinuclear antibody-binding capacity.

3. A diagnostic agent comprising the following peptides:
(a) A peptide consisting of an amino acid sequence shown by Seq. ID No. 2,
(b) A peptide comprising the whole of the amino acid sequence shown by Seq. ID No. 2,
(c) A peptide comprising an amino acid sequence including a part of an amino acid sequence shown by Seq. ID No. 2 and having an antinuclear antibody-binding capacity,
(d) A peptide comprising an amino acid sequence where one or more amino acids are deleted, replaced or added in an amino acid sequence shown by Seq. ID No. 2, and having an antinuclear antibody-binding capacity,
(e) A peptide comprising an amino acid sequence including the whole of the amino acid sequence where one or more amino acids are deleted, replaced or added in an amino acid sequence shown by Seq. ID No. 2, and having an antinuclear antibody-binding capacity, and
(f) A peptide comprising an amino acid sequence including a part of an amino acid sequence where one or more amino acids are deleted, replaced or added in an amino acid sequence shown by Seq. ID No. 2, and having an antinuclear antibody-binding capacity.

4. The diagnostic agent according to paragraph 3, wherein the peptide is a peptide consisting of an amino acid sequence shown by Seq. ID No. 4, or a peptide where one or more amino acids are deleted, replaced or added, and having an antinuclear antibody-binding capacity in an amino acid sequence shown by Seq. ID No. 4.

5. A diagnostic or therapeutic peptide for scleroderma comprising the following peptides:
(a) A peptide consisting of an amino acid sequence shown by Seq. ID No. 2,
(b) A peptide comprising the whole of the amino acid sequence shown by Seq. ID No. 2,
(c) A peptide comprising an amino acid sequence including a part of an amino acid sequence shown by Seq. ID No. 2 and having an antinuclear antibody-binding capacity,
(d) A peptide comprising an amino acid sequence where one or more amino acids are deleted, replaced or added in an amino acid sequence shown by Seq. ID No. 2, and having an antinuclear antibody-binding capacity,
(e) A peptide comprising an amino acid sequence including the whole of the amino acid sequence where one or more amino acids are deleted, replaced or added in an amino acid sequence shown by Seq. ID No. 2, and having an antinuclear antibody-binding capacity, and
(f) A peptide comprising an amino acid sequence including a part of an amino acid sequence where one or more amino acids are deleted, replaced or added in an amino acid sequence shown by Seq. ID No. 2, and having an antinuclear antibody-binding capacity.

6. The diagnostic or therapeutic peptide for scleroderma according to paragraph 5, wherein the peptide is a peptide consisting of an amino acid sequence shown by Seq. ID No. 4, or a peptide comprising an amino acid sequence including the whole of the amino acid where one or more amino acids are deleted, replaced or added in an amino acid sequence shown by Seq. ID No. 4, and having an antinuclear antibody-binding capacity.

7. A monoclonal antibody recognizing the following peptides:
(a) A peptide consisting of an amino acid sequence shown by Seq. ID No. 2,
(b) A peptide comprising the whole of the amino acid sequence shown by Seq. ID No. 2,
(C) A peptide comprising an amino acid sequence including a part of an amino acid sequence shown by Seq. ID No. 2, and having an antinuclear antibody-binding capacity,
(d) A peptide comprising an amino acid sequence where one or more amino acids are deleted, replaced or added in an amino acid sequence shown by Seq. ID No. 2, and having an antinuclear antibody-binding capacity,
(e) A peptide comprising an amino acid sequence including the whole of the amino acid sequence where one or more amino acids are deleted, replaced or added, in an amino acid sequence shown by Seq. ID No. 2, and having an antinuclear antibody-binding capacity, and
(f) A peptide comprising an amino acid sequence including a part of an amino acid sequence where one or more amino acids are deleted, replaced or added in an amino acid sequence shown by Seq. ID No. 2, and having an antinuclear antibody-binding capacity.

8. The monoclonal antibody according to paragraph 7, wherein the peptide is a peptide consisting of an amino acid sequence shown by Seq. ID No. 4, or a peptide comprising an amino acid sequence including the whole of the amino acid sequence where one or more amino acids are deleted, replaced or added in an amino acid sequence shown by Seq. ID No. 4, and having an antinuclear antibody-binding capacity.

9. An anti-idiotypic antibody against the monoclonal antibody according to paragraph 7 or 8.

10. The anti-idiotypic antibody according to paragraph 9, that is diagnosis or therapy for scleroderma.

INDUSTRIAL APPLICABILITY

The present invention has allowed the identification of epitope sites of RNAP subunits recognized commonly by anti-RNAP antibodies in the sera from patients suffering from scleroderma, and made it possible to develop a convenient method of detecting anti-RNAP antibodies by ELISA and the like, by using recombinant proteins including such epitopic region. It is thought to contribute to improvement of the life prognosis of patients suffering from scleroderma, when the measurement of anti-RNAP antibodies becomes possible in general clinical laboratories by providing the present method of detecting as a kit.

The invention claimed is:

1. A method of detecting an anti-RNA polymerase antibody, wherein each of the following peptides are contacted with a sample and the binding of the peptides with an anti-RNA polymerase antibody in the sample is investigated:
   (a) a peptide consisting of the amino acid sequence shown by SEQ ID NO: 2,
   (b) A peptide consisting of the amino acid sequence shown by SEQ ID NO: 4,
   (c) A peptide consisting of the amino acid sequence shown by SEQ ID NO: 12,
   (d) A peptide consisting of amino acid residue numbers 732-1080 in the amino acid sequence shown by SEQ ID NO: 6,
   (e) A peptide consisting of amino acid residue numbers 891-1166 in the amino acid sequence shown by SEQ ID NO: 6.

2. A diagnostic agent for scleroderma comprising each of the following peptides:
   (a) a peptide consisting of the amino acid sequence shown by SEQ ID NO: 2,
   (b) A peptide consisting of the amino acid sequence shown by SEQ ID NO: 4,
   (c) A peptide consisting of the amino acid sequence shown by SEQ ID NO: 12,
   (d) A peptide consisting of amino acid residue numbers 732-1080 in the amino acid sequence shown by SEQ ID NO: 6,
   (e) A peptide consisting of amino acid residue numbers 891-1166 in the amino acid sequence shown by SEQ ID NO: 6.

3. A diagnostic peptide for scleroderma comprising each of the following peptides:
   (a) a peptide consisting of the amino acid sequence shown by SEQ ID NO: 2,
   (b) A peptide consisting of the amino acid sequence shown by SEQ ID NO: 4,
   (c) A peptide consisting of the amino acid sequence shown by SEQ ID NO: 12,
   (d) A peptide consisting of amino acid residue numbers 732-1080 in the amino acid sequence shown by SEQ ID NO: 6,
   (e) A peptide consisting of amino acid residue numbers 891-1166 in the amino acid sequence shown by SEQ ID NO: 6.

4. An isolated monoclonal antibody recognizing the following peptides:
   (a) a peptide consisting of the amino acid sequence shown by SEQ ID NO: 2,
   (b) A peptide consisting of the amino acid sequence shown by SEQ ID NO:4,
   (c) A peptide consisting of the amino acid sequence shown by SEQ ID NO: 12,
   (d) A peptide consisting of amino acid residue numbers 732-1080 in the amino acid sequence shown by SEQ ID NO: 6,
   (e) A peptide consisting of amino acid residue numbers 891-1166 in the amino acid sequence shown by SEQ ID NO: 6.

5. An anti-idiotypic antibody against the monoclonal antibody according to claim 4.

6. A peptide consisting of the amino acid sequence shown by SEQ ID NO:4.

* * * * *

SEQUENCE LISTING

<160> NUMBER OF SEQ ID NOS: 48

<210> SEQ ID NO 1
<211> LENGTH: 390
<212> TYPE: DNA
<213> ORGANISM: Homo sapiens
<220> FEATURE:
<221> NAME/KEY: CDS
<222> LOCATION: (1)..(390)

<400> SEQUENCE: 1

```
cga agc tct act ggc gat att atc cag ttc att tat gga gga gat ggc        48
Arg Ser Ser Thr Gly Asp Ile Ile Gln Phe Ile Tyr Gly Gly Asp Gly
  1               5                  10                  15 tta gat cct gca gct atg gag gga aaa gat gaa cct ttg gag ttt aaa        96
Leu Asp Pro Ala Ala Met Glu Gly Lys Asp Glu Pro Leu Glu Phe Lys
             20                  25                  30 agg gtt ctg gac aac atc aaa gca gtc ttc ccg tgt ccc agt gag cct       144
Arg Val Leu Asp Asn Ile Lys Ala Val Phe Pro Cys Pro Ser Glu Pro
         35                  40                  45 gct ctc agc aaa aac gag ctg atc ctg acc aca gag tcc atc atg aag       192
Ala Leu Ser Lys Asn Glu Leu Ile Leu Thr Thr Glu Ser Ile Met Lys
     50                  55                  60 aag agt gag ttc ctc tgc tgc cag gac agc ttc ctg cag gaa ata aaa       240
Lys Ser Glu Phe Leu Cys Cys Gln Asp Ser Phe Leu Gln Glu Ile Lys
 65                  70                  75                  80 aaa ttc att aag ggg gtc tct gag aag atc aag aaa acc aga gat aaa       288
Lys Phe Ile Lys Gly Val Ser Glu Lys Ile Lys Lys Thr Arg Asp Lys
                 85                  90                  95 tat ggc atc aat gat aac ggc aca aca gag ccc cgt gtg ctg tac cag       336
Tyr Gly Ile Asn Asp Asn Gly Thr Thr Glu Pro Arg Val Leu Tyr Gln
            100                 105                 110 ctg gac cgc atc acc ccc acc caa gta gaa aag ttt ctg gag acc tgt       384
Leu Asp Arg Ile Thr Pro Thr Gln Val Glu Lys Phe Leu Glu Thr Cys
        115                 120                 125 agg gac                                                                390
Arg Asp
    130
```

<210> SEQ ID NO 2
<211> LENGTH: 130
<212> TYPE: PRT
<213> ORGANISM: Homo sapiens

<400> SEQUENCE: 2

```
Arg Ser Ser Thr Gly Asp Ile Ile Gln Phe Ile Tyr Gly Gly Asp Gly
  1               5                  10                  15

Leu Asp Pro Ala Ala Met Glu Gly Lys Asp Glu Pro Leu Glu Phe Lys
             20                  25                  30

Arg Val Leu Asp Asn Ile Lys Ala Val Phe Pro Cys Pro Ser Glu Pro
         35                  40                  45

Ala Leu Ser Lys Asn Glu Leu Ile Leu Thr Thr Glu Ser Ile Met Lys
     50                  55                  60

Lys Ser Glu Phe Leu Cys Cys Gln Asp Ser Phe Leu Gln Glu Ile Lys
 65                  70                  75                  80

Lys Phe Ile Lys Gly Val Ser Glu Lys Ile Lys Lys Thr Arg Asp Lys
                 85                  90                  95

Tyr Gly Ile Asn Asp Asn Gly Thr Thr Glu Pro Arg Val Leu Tyr Gln
            100                 105                 110
```

```
Leu Asp Arg Ile Thr Pro Thr Gln Val Glu Lys Phe Leu Glu Thr Cys
        115                 120                 125

Arg Asp
    130

<210> SEQ ID NO 3
<211> LENGTH: 570
<212> TYPE: DNA
<213> ORGANISM: Homo sapiens
<220> FEATURE:
<221> NAME/KEY: CDS
<222> LOCATION: (1)..(570)

<400> SEQUENCE: 3 cga agc tct act ggc gat att atc cag ttc att tat gga gga gat ggc     48
Arg Ser Ser Thr Gly Asp Ile Ile Gln Phe Ile Tyr Gly Gly Asp Gly
  1               5                  10                  15 tta gat cct gca gct atg gag gga aaa gat gaa cct ttg gag ttt aaa     96
Leu Asp Pro Ala Ala Met Glu Gly Lys Asp Glu Pro Leu Glu Phe Lys
             20                  25                  30 agg gtt ctg gac aac atc aaa gca gtc ttc ccg tgt ccc agt gag cct    144
Arg Val Leu Asp Asn Ile Lys Ala Val Phe Pro Cys Pro Ser Glu Pro
         35                  40                  45 gct ctc agc aaa aac gag ctg atc ctg acc aca gag tcc atc atg aag    192
Ala Leu Ser Lys Asn Glu Leu Ile Leu Thr Thr Glu Ser Ile Met Lys
     50                  55                  60 aag agt gag ttc ctc tgc tgc cag gac agc ttc ctg cag gaa ata aaa    240
Lys Ser Glu Phe Leu Cys Cys Gln Asp Ser Phe Leu Gln Glu Ile Lys
 65                  70                  75                  80 aaa ttc att aag ggg gtc tct gag aag atc aag aaa acc aga gat aaa    288
Lys Phe Ile Lys Gly Val Ser Glu Lys Ile Lys Lys Thr Arg Asp Lys
                 85                  90                  95 tat ggc atc aat gat aac ggc aca aca gag ccc cgt gtg ctg tac cag    336
Tyr Gly Ile Asn Asp Asn Gly Thr Thr Glu Pro Arg Val Leu Tyr Gln
            100                 105                 110 ctg gac cgc atc acc ccc acc caa gta gaa aag ttt ctg gag acc tgt    384
Leu Asp Arg Ile Thr Pro Thr Gln Val Glu Lys Phe Leu Glu Thr Cys
        115                 120                 125 agg gac aag tac atg agg gca cag atg gag cct ggt tct gca gtg ggt    432
Arg Asp Lys Tyr Met Arg Ala Gln Met Glu Pro Gly Ser Ala Val Gly
    130                 135                 140 gct ctg tgt gcc cag agc att ggt gag cca ggc acc cag atg acc ctg    480
Ala Leu Cys Ala Gln Ser Ile Gly Glu Pro Gly Thr Gln Met Thr Leu
145                 150                 155                 160 aag act ttc cac ttt gca ggt gtg gcc tcc atg aac atc acc ctg ggc    528
Lys Thr Phe His Phe Ala Gly Val Ala Ser Met Asn Ile Thr Leu Gly
                165                 170                 175 gtg ccc cgg att aaa gag atc atc aac gct tcc aag gcc atc                570
Val Pro Arg Ile Lys Glu Ile Ile Asn Ala Ser Lys Ala Ile
            180                 185                 190

<210> SEQ ID NO 4
<211> LENGTH: 190
<212> TYPE: PRT
<213> ORGANISM: Homo sapiens

<400> SEQUENCE: 4

Arg Ser Ser Thr Gly Asp Ile Ile Gln Phe Ile Tyr Gly Gly Asp Gly
  1               5                  10                  15

Leu Asp Pro Ala Ala Met Glu Gly Lys Asp Glu Pro Leu Glu Phe Lys
             20                  25                  30
```

```
Arg Val Leu Asp Asn Ile Lys Ala Val Phe Pro Cys Pro Ser Glu Pro
             35                  40                  45

Ala Leu Ser Lys Asn Glu Leu Ile Leu Thr Thr Glu Ser Ile Met Lys
 50                  55                  60

Lys Ser Glu Phe Leu Cys Cys Gln Asp Ser Phe Leu Gln Glu Ile Lys
 65                  70                  75                  80

Lys Phe Ile Lys Gly Val Ser Glu Lys Ile Lys Lys Thr Arg Asp Lys
                 85                  90                  95

Tyr Gly Ile Asn Asp Asn Gly Thr Thr Glu Pro Arg Val Leu Tyr Gln
                100                 105                 110

Leu Asp Arg Ile Thr Pro Thr Gln Val Glu Lys Phe Leu Glu Thr Cys
            115                 120                 125

Arg Asp Lys Tyr Met Arg Ala Gln Met Glu Pro Gly Ser Ala Val Gly
130                 135                 140

Ala Leu Cys Ala Gln Ser Ile Gly Glu Pro Gly Thr Gln Met Thr Leu
145                 150                 155                 160

Lys Thr Phe His Phe Ala Gly Val Ala Ser Met Asn Ile Thr Leu Gly
                165                 170                 175

Val Pro Arg Ile Lys Glu Ile Ile Asn Ala Ser Lys Ala Ile
                180                 185                 190

<210> SEQ ID NO 5
<211> LENGTH: 4176
<212> TYPE: DNA
<213> ORGANISM: Homo sapiens
<220> FEATURE:
<221> NAME/KEY: CDS
<222> LOCATION: (1)..(4176)

<400> SEQUENCE: 5 atg gtg aag gag cag ttc cgg gag acg gat gtg gcc aag aaa aca agc      48
Met Val Lys Glu Gln Phe Arg Glu Thr Asp Val Ala Lys Lys Thr Ser
 1               5                  10                  15 cac atc tgt ttt gga atg aag tca cct gag gag atg cgc cag cag gcg      96
His Ile Cys Phe Gly Met Lys Ser Pro Glu Glu Met Arg Gln Gln Ala
                 20                  25                  30 cac atc caa gtt gtg agt aag aac ctg tac agc cag gac aac caa cat     144
His Ile Gln Val Val Ser Lys Asn Leu Tyr Ser Gln Asp Asn Gln His
             35                  40                  45 gcc ccc ttg cta tat ggg gtg ctc gac cat agg atg ggt acg agt gag     192
Ala Pro Leu Leu Tyr Gly Val Leu Asp His Arg Met Gly Thr Ser Glu
 50                  55                  60 aag gat cgt cca tgt gaa acc tgt ggg aaa aac ttg gct gac tgt cta     240
Lys Asp Arg Pro Cys Glu Thr Cys Gly Lys Asn Leu Ala Asp Cys Leu
 65                  70                  75                  80 ggc cac tat ggg tat atc gac ctg gag ttg ccg tgt ttt cat gta ggg     288
Gly His Tyr Gly Tyr Ile Asp Leu Glu Leu Pro Cys Phe His Val Gly
                 85                  90                  95 tac ttc aga gca gtc ata ggc atc tta cag atg atc tgc aaa acc tgc     336
Tyr Phe Arg Ala Val Ile Gly Ile Leu Gln Met Ile Cys Lys Thr Cys
                100                 105                 110 tgc cac atc atg ctg tcc caa gag gag aag aag cag ttt ctg gac tat     384
Cys His Ile Met Leu Ser Gln Glu Glu Lys Lys Gln Phe Leu Asp Tyr
            115                 120                 125 cta aag agg ccc ggc ctg acc tac ctt cag aag cga gga ctg aaa aag     432
Leu Lys Arg Pro Gly Leu Thr Tyr Leu Gln Lys Arg Gly Leu Lys Lys
130                 135                 140
```

```
aaa atc tct gac aag tgc cgg aag aaa aac atc tgc cat cac tgt ggc      480
Lys Ile Ser Asp Lys Cys Arg Lys Lys Asn Ile Cys His His Cys Gly
145                 150                 155                 160 gct ttt aat ggt acc gta aag aag tgt gga ctg ctg aaa ata att cat      528
Ala Phe Asn Gly Thr Val Lys Lys Cys Gly Leu Leu Lys Ile Ile His
                165                 170                 175 gag aaa tac aag acc aac aaa aaa gtg gtg gat ccc att gta tca aat      576
Glu Lys Tyr Lys Thr Asn Lys Lys Val Val Asp Pro Ile Val Ser Asn
            180                 185                 190 ttc ctt cag tct ttt gaa aca gcc att gaa cat aat aaa gaa gtg gag      624
Phe Leu Gln Ser Phe Glu Thr Ala Ile Glu His Asn Lys Glu Val Glu
        195                 200                 205 cct ctg ctg gga agg gca cag gaa aac ttg aat ccc tta gta gtt ctg      672
Pro Leu Leu Gly Arg Ala Gln Glu Asn Leu Asn Pro Leu Val Val Leu
    210                 215                 220 aat tta ttt aaa cga atc cca gct gaa gat gtt cct cta ctt ctg atg      720
Asn Leu Phe Lys Arg Ile Pro Ala Glu Asp Val Pro Leu Leu Leu Met
225                 230                 235                 240 aac cca gaa gcc gga aag ccg tct gat ttg att ctc aca cga ctt ttg      768
Asn Pro Glu Ala Gly Lys Pro Ser Asp Leu Ile Leu Thr Arg Leu Leu
                245                 250                 255 gtg cct cct ttg tgt ttc aga ccc tcc gtt gtg agt gat ttg aag tct      816
Val Pro Pro Leu Cys Phe Arg Pro Ser Val Val Ser Asp Leu Lys Ser
            260                 265                 270 ggc acc aat gaa gat gat ctg aca atg aaa ctg aca gaa atc att ttc      864
Gly Thr Asn Glu Asp Asp Leu Thr Met Lys Leu Thr Glu Ile Ile Phe
        275                 280                 285 cta aac gat gtt att aaa aag cat cgg atc tca gga gcc aag acc cag      912
Leu Asn Asp Val Ile Lys Lys His Arg Ile Ser Gly Ala Lys Thr Gln
    290                 295                 300 atg atc atg gag gac tgg gat ttc ctg cag ctg cag tgt gcc ctc tac      960
Met Ile Met Glu Asp Trp Asp Phe Leu Gln Leu Gln Cys Ala Leu Tyr
305                 310                 315                 320 att aac agt gag ctc tcg ggc att ccc ctc aac atg gca ccc aag aag     1008
Ile Asn Ser Glu Leu Ser Gly Ile Pro Leu Asn Met Ala Pro Lys Lys
                325                 330                 335 tgg acc aga ggc ttc gtc caa cgc ctg aag gga aaa cag ggt cga ttt     1056
Trp Thr Arg Gly Phe Val Gln Arg Leu Lys Gly Lys Gln Gly Arg Phe
            340                 345                 350 aga gga aat ctc tca gga aag aga gtg gat ttt tct ggc aga aca gtc     1104
Arg Gly Asn Leu Ser Gly Lys Arg Val Asp Phe Ser Gly Arg Thr Val
        355                 360                 365 atc tcg ccc gac ccc aac ctc cgg att gat gag gta gct gtg cca gtt     1152
Ile Ser Pro Asp Pro Asn Leu Arg Ile Asp Glu Val Ala Val Pro Val
    370                 375                 380 cat gtg gcc aaa att cta act ttt cct gag aag gta aac aaa gca aac     1200
His Val Ala Lys Ile Leu Thr Phe Pro Glu Lys Val Asn Lys Ala Asn
385                 390                 395                 400 atc aat ttc ttg agg aaa ctg gtt caa aac ggc cct gag gtt cac cca     1248
Ile Asn Phe Leu Arg Lys Leu Val Gln Asn Gly Pro Glu Val His Pro
                405                 410                 415 gga gca aac ttc att cag cag aga cat acg cag atg aaa agg ttt ttg     1296
Gly Ala Asn Phe Ile Gln Gln Arg His Thr Gln Met Lys Arg Phe Leu
            420                 425                 430 aaa tac gga aat cga gaa aag atg gct caa gag ctc aag tat ggt gac     1344
Lys Tyr Gly Asn Arg Glu Lys Met Ala Gln Glu Leu Lys Tyr Gly Asp
        435                 440                 445 atc gta gag aga cac ctc atc gat gga gat gtg gtg ctg ttc aat cgg     1392
Ile Val Glu Arg His Leu Ile Asp Gly Asp Val Val Leu Phe Asn Arg
    450                 455                 460
```

```
cag ccc tcg ctg cac aaa ttg agc att atg gct cat ctg gcc agg gtc       1440
Gln Pro Ser Leu His Lys Leu Ser Ile Met Ala His Leu Ala Arg Val
465                 470                 475                 480 aag ccc cac cgg acc ttc aga ttt aat gag tgt gtc tgt aca ccc tat       1488
Lys Pro His Arg Thr Phe Arg Phe Asn Glu Cys Val Cys Thr Pro Tyr
                485                 490                 495 aat gct gac ttt gat ggt gat gaa atg aac ctt cat ctt cct caa aca       1536
Asn Ala Asp Phe Asp Gly Asp Glu Met Asn Leu His Leu Pro Gln Thr
            500                 505                 510 gaa gaa gct aaa gca gag gcc ctt gtt ctg atg ggg act aaa gca aat       1584
Glu Glu Ala Lys Ala Glu Ala Leu Val Leu Met Gly Thr Lys Ala Asn
        515                 520                 525 ctt gta acc ccg agg aat ggg gaa ccg ctg att gct gct att cag gat       1632
Leu Val Thr Pro Arg Asn Gly Glu Pro Leu Ile Ala Ala Ile Gln Asp
    530                 535                 540 ttt cta aca ggt gcc tat ctc ctc act ctc aag gac act ttc ttt gat       1680
Phe Leu Thr Gly Ala Tyr Leu Leu Thr Leu Lys Asp Thr Phe Phe Asp
545                 550                 555                 560 cga gcc aag gct tgc caa atc att gct tca ata ctg gtt ggc aag gat       1728
Arg Ala Lys Ala Cys Gln Ile Ile Ala Ser Ile Leu Val Gly Lys Asp
                565                 570                 575 gag aaa att aaa gtt cgc ctc cca ccg cct aca atc cta aag cct gtc       1776
Glu Lys Ile Lys Val Arg Leu Pro Pro Pro Thr Ile Leu Lys Pro Val
            580                 585                 590 acc ctg tgg acg gga aag cag atc ttc agt gtc atc ctc agg cct agc       1824
Thr Leu Trp Thr Gly Lys Gln Ile Phe Ser Val Ile Leu Arg Pro Ser
        595                 600                 605 gat gac aat cca gtg agg gcc aac ctg cga acc aag ggc aag cag tac       1872
Asp Asp Asn Pro Val Arg Ala Asn Leu Arg Thr Lys Gly Lys Gln Tyr
    610                 615                 620 tgt ggc aaa ggg gaa gat ctc tgt gcc aat gat tcc tat gtt aca atc       1920
Cys Gly Lys Gly Glu Asp Leu Cys Ala Asn Asp Ser Tyr Val Thr Ile
625                 630                 635                 640 cag aac agt gag ttg atg agt ggc agc atg gac aaa gga acc cta ggg       1968
Gln Asn Ser Glu Leu Met Ser Gly Ser Met Asp Lys Gly Thr Leu Gly
                645                 650                 655 tca gga tcc aag aac aat att ttt tac att ttg ctg cga gac tgg gga       2016
Ser Gly Ser Lys Asn Asn Ile Phe Tyr Ile Leu Leu Arg Asp Trp Gly
            660                 665                 670 cag aat gaa gct gca gat gcc atg tca cgg ctc gcc agg ctg gct cct       2064
Gln Asn Glu Ala Ala Asp Ala Met Ser Arg Leu Ala Arg Leu Ala Pro
        675                 680                 685 gtc tac ctg tct aac cgt ggt ttc tca att ggg atc ggt gat gtc aca       2112
Val Tyr Leu Ser Asn Arg Gly Phe Ser Ile Gly Ile Gly Asp Val Thr
    690                 695                 700 cct ggc caa gga ctg ctg aag gcc aag tat gag ttg ctg aat gcc ggc       2160
Pro Gly Gln Gly Leu Leu Lys Ala Lys Tyr Glu Leu Leu Asn Ala Gly
705                 710                 715                 720 tac aag aaa tgt gat gag tac atc gaa gcc ctg aac acg ggc aag ctg       2208
Tyr Lys Lys Cys Asp Glu Tyr Ile Glu Ala Leu Asn Thr Gly Lys Leu
                725                 730                 735 cag cag cag cct ggc tgc act gct gag gag acc ctg gag gca ctg atc       2256
Gln Gln Gln Pro Gly Cys Thr Ala Glu Glu Thr Leu Glu Ala Leu Ile
            740                 745                 750 ctg aag gag ctg tct gtg atc cgt gac cac gct ggc agt gcc tgc ctc       2304
Leu Lys Glu Leu Ser Val Ile Arg Asp His Ala Gly Ser Ala Cys Leu
        755                 760                 765 cgg gag ctg gac aag agc aac agc ccc ctc acc atg gct ctg tgc ggc       2352
Arg Glu Leu Asp Lys Ser Asn Ser Pro Leu Thr Met Ala Leu Cys Gly
```

|     |     |
| --- | --- |
| tcc aaa ggt tcc ttc att aac ata tca cag atg att gcc tgt gtg gga<br>Ser Lys Gly Ser Phe Ile Asn Ile Ser Gln Met Ile Ala Cys Val Gly<br>785                   790                 795                  800 | 2400 |
| cag cag gcc atc agt ggc tct cga gtg cca gac ggc ttt gaa aac agg<br>Gln Gln Ala Ile Ser Gly Ser Arg Val Pro Asp Gly Phe Glu Asn Arg<br>                  805                 810                 815 | 2448 |
| tcc ttg cct cat ttt gaa aaa cac tca aag ctc cca gct gcc aaa ggc<br>Ser Leu Pro His Phe Glu Lys His Ser Lys Leu Pro Ala Ala Lys Gly<br>   820                  825                 830 | 2496 |
| ttt gtg gct aat agc ttt tat tcc ggt ttg aca cca act gag ttt ttc<br>Phe Val Ala Asn Ser Phe Tyr Ser Gly Leu Thr Pro Thr Glu Phe Phe<br>835                   840                 845 | 2544 |
| ttc cac aca atg gcc ggc cgg gaa ggt cta gtc gac acg gct gta aag<br>Phe His Thr Met Ala Gly Arg Glu Gly Leu Val Asp Thr Ala Val Lys<br>                  850                 855                 860 | 2592 |
| aca gct gaa acg gga tac atg cag cga agg ctt gtc aaa tct ctt gaa<br>Thr Ala Glu Thr Gly Tyr Met Gln Arg Arg Leu Val Lys Ser Leu Glu<br>865                   870                 875                 880 | 2640 |
| gat ctt tgc tcc cag tat gat ctg aca gtc cga agc tct act ggc gat<br>Asp Leu Cys Ser Gln Tyr Asp Leu Thr Val Arg Ser Ser Thr Gly Asp<br>                  885                 890                 895 | 2688 |
| att atc cag ttc att tat gga gga gat ggc tta gat cct gca gct atg<br>Ile Ile Gln Phe Ile Tyr Gly Gly Asp Gly Leu Asp Pro Ala Ala Met<br>   900                  905                 910 | 2736 |
| gag gga aaa gat gaa cct ttg gag ttt aaa agg gtt ctg gac aac atc<br>Glu Gly Lys Asp Glu Pro Leu Glu Phe Lys Arg Val Leu Asp Asn Ile<br>915                   920                 925 | 2784 |
| aaa gca gtc ttc ccg tgt ccc agt gag cct gct ctc agc aaa aac gag<br>Lys Ala Val Phe Pro Cys Pro Ser Glu Pro Ala Leu Ser Lys Asn Glu<br>   930                  935                 940 | 2832 |
| ctg atc ctg acc aca gag tcc atc atg aag aag agt gag ttc ctc tgc<br>Leu Ile Leu Thr Thr Glu Ser Ile Met Lys Lys Ser Glu Phe Leu Cys<br>945                   950                 955                 960 | 2880 |
| tgc cag gac agc ttc ctg cag gaa ata aaa aaa ttc att aag ggg gtc<br>Cys Gln Asp Ser Phe Leu Gln Glu Ile Lys Lys Phe Ile Lys Gly Val<br>                  965                 970                 975 | 2928 |
| tct gag aag atc aag aaa acc aga gat aaa tat ggc atc aat gat aac<br>Ser Glu Lys Ile Lys Lys Thr Arg Asp Lys Tyr Gly Ile Asn Asp Asn<br>   980                  985                 990 | 2976 |
| ggc aca aca gag ccc cgt gtg ctg tac cag ctg gac cgc atc acc ccc<br>Gly Thr Thr Glu Pro Arg Val Leu Tyr Gln Leu Asp Arg Ile Thr Pro<br>995                   1000                1005 | 3024 |
| acc caa gta gaa aag ttt ctg gag acc tgt agg gac aag tac atg agg<br>Thr Gln Val Glu Lys Phe Leu Glu Thr Cys Arg Asp Lys Tyr Met Arg<br>  1010                1015                1020 | 3072 |
| gca cag atg gag cca ggt tct gca gtg ggt gct ctg tgt gcc cag agc<br>Ala Gln Met Glu Pro Gly Ser Ala Val Gly Ala Leu Cys Ala Gln Ser<br>1025                1030                1035                1040 | 3120 |
| att ggt gag cca ggc acc cag atg acc ctg aag act ttc cac ttt gga<br>Ile Gly Glu Pro Gly Thr Gln Met Thr Leu Lys Thr Phe His Phe Gly<br>                  1045                1050                1055 | 3168 |
| ggt gtg gcc tcc atg aac atc acc ctg ggc gtg ccc cgg att aaa gag<br>Gly Val Ala Ser Met Asn Ile Thr Leu Gly Val Pro Arg Ile Lys Glu<br>           1060                1065                1070 | 3216 |
| atc atc aac gct tcc aag gcc atc agc act cca att atc aca gca cag<br>Ile Ile Asn Ala Ser Lys Ala Ile Ser Thr Pro Ile Ile Thr Ala Gln<br>  1075                1080                1085 | 3264 |
| cta gac aag gat gac gac gcg gat tat gct cgc ctc gtg aaa ggg aga | 3312 |

```
Leu Asp Lys Asp Asp Ala Asp Tyr Ala Arg Leu Val Lys Gly Arg
    1090                1095                1100 att gag aaa acc ctc ttg gga gag att tcc gag tat att gaa gaa gtg    3360
Ile Glu Lys Thr Leu Leu Gly Glu Ile Ser Glu Tyr Ile Glu Glu Val
1105                1110                1115                1120 ttt ctt cct gat gac tgc ttt att ctc gtc aag ctc tcc ctg gaa cgg    3408
Phe Leu Pro Asp Asp Cys Phe Ile Leu Val Lys Leu Ser Leu Glu Arg
                1125                1130                1135 att agg ctt ctg aga ctg gaa gtg aac gct gag aca gtg aga tat tcc    3456
Ile Arg Leu Leu Arg Leu Glu Val Asn Ala Glu Thr Val Arg Tyr Ser
            1140                1145                1150 atc tgc aca tcc aag ctc cgt gtg aag ccc ggt gat gtg gct gtt cat    3504
Ile Cys Thr Ser Lys Leu Arg Val Lys Pro Gly Asp Val Ala Val His
        1155                1160                1165 ggt gag gct gtg gtg tgt gtc acc ccc aga gag aac agc aag agc tcc    3552
Gly Glu Ala Val Val Cys Val Thr Pro Arg Glu Asn Ser Lys Ser Ser
    1170                1175                1180 atg tac tac gtg ctg cag ttc ctg aaa gag gat ctc ccc aag gtg gtg    3600
Met Tyr Tyr Val Leu Gln Phe Leu Lys Glu Asp Leu Pro Lys Val Val
1185                1190                1195                1200 gtg cag ggc att cca gag gtg tcc aga gct gtc atc cac att gac gag    3648
Val Gln Gly Ile Pro Glu Val Ser Arg Ala Val Ile His Ile Asp Glu
                1205                1210                1215 cag agt gga aag gag aag tac aag ctt ctg gtg gaa ggt gat aac ctg    3696
Gln Ser Gly Lys Glu Lys Tyr Lys Leu Leu Val Glu Gly Asp Asn Leu
            1220                1225                1230 cgg gca gtc atg gcc aca cac ggt gtg aag ggc acc cga acc acc tcc    3744
Arg Ala Val Met Ala Thr His Gly Val Lys Gly Thr Arg Thr Thr Ser
        1235                1240                1245 aat aac acc tat gag gtg gag aaa act ctg ggc atc gag gcc gcc cgg    3792
Asn Asn Thr Tyr Glu Val Glu Lys Thr Leu Gly Ile Glu Ala Ala Arg
    1250                1255                1260 aca acg atc atc aat gaa atc cag tac acc atg gtg gtg aac cac ggc    3840
Thr Thr Ile Ile Asn Glu Ile Gln Tyr Thr Met Val Val Asn His Gly
1265                1270                1275                1280 atg agc atc gac agg agg cac gtg atg ctg ctc tcc gac ctc atg acc    3888
Met Ser Ile Asp Arg Arg His Val Met Leu Leu Ser Asp Leu Met Thr
                1285                1290                1295 tac aag ggt gaa gtc ctg ggc atc act agg ttt ggc ctg gcc aag atg    3936
Tyr Lys Gly Glu Val Leu Gly Ile Thr Arg Phe Gly Leu Ala Lys Met
            1300                1305                1310 aag gag agt gtg ctg atg ctg gcc tcc ttt gag aag acg gct gac cat    3984
Lys Glu Ser Val Leu Met Leu Ala Ser Phe Glu Lys Thr Ala Asp His
        1315                1320                1325 ctc ttt gac gct gcc tac ttc ggg cag aag gac tct gtg tgt ggg gtg    4032
Leu Phe Asp Ala Ala Tyr Phe Gly Gln Lys Asp Ser Val Cys Gly Val
    1330                1335                1340 tct gag tgc atc atc atg gga atc cca atg aac att gga acc ggg ctc    4080
Ser Glu Cys Ile Ile Met Gly Ile Pro Met Asn Ile Gly Thr Gly Leu
1345                1350                1355                1360 ttc aag ctg ctt cac aag gct gac agg gac ccg aac cct ccc aag agg    4128
Phe Lys Leu Leu His Lys Ala Asp Arg Asp Pro Asn Pro Pro Lys Arg
                1365                1370                1375 ccc ctg atc ttc gac aca aat gaa ttc cac atc ccc ctt gtc aca tag    4176
Pro Leu Ile Phe Asp Thr Asn Glu Phe His Ile Pro Leu Val Thr
            1380                1385                1390

<210> SEQ ID NO 6
<211> LENGTH: 1391
<212> TYPE: PRT
```

<213> ORGANISM: Homo sapiens

<400> SEQUENCE: 6

```
Met Val Lys Glu Gln Phe Arg Glu Thr Asp Val Ala Lys Lys Thr Ser
 1               5                  10                  15
His Ile Cys Phe Gly Met Lys Ser Pro Glu Glu Met Arg Gln Gln Ala
                20                  25                  30
His Ile Gln Val Val Ser Lys Asn Leu Tyr Ser Gln Asp Asn Gln His
            35                  40                  45
Ala Pro Leu Leu Tyr Gly Val Leu Asp His Arg Met Gly Thr Ser Glu
        50                  55                  60
Lys Asp Arg Pro Cys Glu Thr Cys Gly Lys Asn Leu Ala Asp Cys Leu
65                  70                  75                  80
Gly His Tyr Gly Tyr Ile Asp Leu Glu Leu Pro Cys Phe His Val Gly
                85                  90                  95
Tyr Phe Arg Ala Val Ile Gly Ile Leu Gln Met Ile Cys Lys Thr Cys
                100                 105                 110
Cys His Ile Met Leu Ser Gln Glu Glu Lys Lys Gln Phe Leu Asp Tyr
            115                 120                 125
Leu Lys Arg Pro Gly Leu Thr Tyr Leu Gln Lys Arg Gly Leu Lys Lys
        130                 135                 140
Lys Ile Ser Asp Lys Cys Arg Lys Lys Asn Ile Cys His His Cys Gly
145                 150                 155                 160
Ala Phe Asn Gly Thr Val Lys Lys Cys Gly Leu Leu Lys Ile Ile His
                165                 170                 175
Glu Lys Tyr Lys Thr Asn Lys Lys Val Val Asp Pro Ile Val Ser Asn
                180                 185                 190
Phe Leu Gln Ser Phe Glu Thr Ala Ile Glu His Asn Lys Glu Val Glu
            195                 200                 205
Pro Leu Leu Gly Arg Ala Gln Glu Asn Leu Asn Pro Leu Val Val Leu
        210                 215                 220
Asn Leu Phe Lys Arg Ile Pro Ala Glu Asp Val Pro Leu Leu Leu Met
225                 230                 235                 240
Asn Pro Glu Ala Gly Lys Pro Ser Asp Leu Ile Leu Thr Arg Leu Leu
                245                 250                 255
Val Pro Pro Leu Cys Phe Arg Pro Ser Val Val Ser Asp Leu Lys Ser
                260                 265                 270
Gly Thr Asn Glu Asp Asp Leu Thr Met Lys Leu Thr Glu Ile Ile Phe
            275                 280                 285
Leu Asn Asp Val Ile Lys Lys His Arg Ile Ser Gly Ala Lys Thr Gln
        290                 295                 300
Met Ile Met Glu Asp Trp Asp Phe Leu Gln Leu Gln Cys Ala Leu Tyr
305                 310                 315                 320
Ile Asn Ser Glu Leu Ser Gly Ile Pro Leu Asn Met Ala Pro Lys Lys
                325                 330                 335
Trp Thr Arg Gly Phe Val Gln Arg Leu Lys Gly Lys Gln Gly Arg Phe
                340                 345                 350
Arg Gly Asn Leu Ser Gly Lys Arg Val Asp Phe Ser Gly Arg Thr Val
            355                 360                 365
Ile Ser Pro Asp Pro Asn Leu Arg Ile Asp Glu Val Ala Val Pro Val
        370                 375                 380
His Val Ala Lys Ile Leu Thr Phe Pro Glu Lys Val Asn Lys Ala Asn
385                 390                 395                 400
```

-continued

```
Ile Asn Phe Leu Arg Lys Leu Val Gln Asn Gly Pro Glu Val His Pro
            405                 410                 415
Gly Ala Asn Phe Ile Gln Gln Arg His Thr Gln Met Lys Arg Phe Leu
        420                 425                 430
Lys Tyr Gly Asn Arg Glu Lys Met Ala Gln Glu Leu Lys Tyr Gly Asp
        435                 440                 445
Ile Val Glu Arg His Leu Ile Asp Gly Asp Val Val Leu Phe Asn Arg
    450                 455                 460
Gln Pro Ser Leu His Lys Leu Ser Ile Met Ala His Leu Ala Arg Val
465                 470                 475                 480
Lys Pro His Arg Thr Phe Arg Phe Asn Glu Cys Val Cys Thr Pro Tyr
                485                 490                 495
Asn Ala Asp Phe Asp Gly Asp Glu Met Asn Leu His Leu Pro Gln Thr
                500                 505                 510
Glu Glu Ala Lys Ala Glu Ala Leu Val Leu Met Gly Thr Lys Ala Asn
        515                 520                 525
Leu Val Thr Pro Arg Asn Gly Glu Pro Leu Ile Ala Ala Ile Gln Asp
    530                 535                 540
Phe Leu Thr Gly Ala Tyr Leu Leu Thr Leu Lys Asp Thr Phe Phe Asp
545                 550                 555                 560
Arg Ala Lys Ala Cys Gln Ile Ile Ala Ser Ile Leu Val Gly Lys Asp
                565                 570                 575
Glu Lys Ile Lys Val Arg Leu Pro Pro Thr Ile Leu Lys Pro Val
        580                 585                 590
Thr Leu Trp Thr Gly Lys Gln Ile Phe Ser Val Ile Leu Arg Pro Ser
    595                 600                 605
Asp Asp Asn Pro Val Arg Ala Asn Leu Arg Thr Lys Gly Lys Gln Tyr
610                 615                 620
Cys Gly Lys Gly Glu Asp Leu Cys Ala Asn Asp Ser Tyr Val Thr Ile
625                 630                 635                 640
Gln Asn Ser Glu Leu Met Ser Gly Ser Met Asp Lys Gly Thr Leu Gly
                645                 650                 655
Ser Gly Ser Lys Asn Asn Ile Phe Tyr Ile Leu Leu Arg Asp Trp Gly
                660                 665                 670
Gln Asn Glu Ala Ala Asp Ala Met Ser Arg Leu Ala Arg Leu Ala Pro
            675                 680                 685
Val Tyr Leu Ser Asn Arg Gly Phe Ser Ile Gly Ile Gly Asp Val Thr
        690                 695                 700
Pro Gly Gln Gly Leu Leu Lys Ala Lys Tyr Glu Leu Leu Asn Ala Gly
705                 710                 715                 720
Tyr Lys Lys Cys Asp Glu Tyr Ile Glu Ala Leu Asn Thr Gly Lys Leu
                725                 730                 735
Gln Gln Gln Pro Gly Cys Thr Ala Glu Glu Thr Leu Glu Ala Leu Ile
            740                 745                 750
Leu Lys Glu Leu Ser Val Ile Arg Asp His Ala Gly Ser Ala Cys Leu
        755                 760                 765
Arg Glu Leu Asp Lys Ser Asn Ser Pro Leu Thr Met Ala Leu Cys Gly
    770                 775                 780
Ser Lys Gly Ser Phe Ile Asn Ile Ser Gln Met Ile Ala Cys Val Gly
785                 790                 795                 800
Gln Gln Ala Ile Ser Gly Ser Arg Val Pro Asp Gly Phe Glu Asn Arg
                805                 810                 815
Ser Leu Pro His Phe Glu Lys His Ser Lys Leu Pro Ala Ala Lys Gly
```

-continued

```
                820                 825                 830
Phe Val Ala Asn Ser Phe Tyr Ser Gly Leu Thr Pro Thr Glu Phe Phe
                835                 840                 845
Phe His Thr Met Ala Gly Arg Glu Gly Leu Val Asp Thr Ala Val Lys
                850                 855                 860
Thr Ala Glu Thr Gly Tyr Met Gln Arg Arg Leu Val Lys Ser Leu Glu
865                 870                 875                 880
Asp Leu Cys Ser Gln Tyr Asp Leu Thr Val Arg Ser Ser Thr Gly Asp
                885                 890                 895
Ile Ile Gln Phe Ile Tyr Gly Gly Asp Gly Leu Asp Pro Ala Ala Met
                900                 905                 910
Glu Gly Lys Asp Glu Pro Leu Glu Phe Lys Arg Val Leu Asp Asn Ile
                915                 920                 925
Lys Ala Val Phe Pro Cys Pro Ser Glu Pro Ala Leu Ser Lys Asn Glu
                930                 935                 940
Leu Ile Leu Thr Thr Glu Ser Ile Met Lys Lys Ser Glu Phe Leu Cys
945                 950                 955                 960
Cys Gln Asp Ser Phe Leu Gln Glu Ile Lys Lys Phe Ile Lys Gly Val
                965                 970                 975
Ser Glu Lys Ile Lys Lys Thr Arg Asp Lys Tyr Gly Ile Asn Asp Asn
                980                 985                 990
Gly Thr Thr Glu Pro Arg Val Leu Tyr Gln Leu Asp Arg Ile Thr Pro
                995                 1000                1005
Thr Gln Val Glu Lys Phe Leu Glu Thr Cys Arg Asp Lys Tyr Met Arg
    1010                1015                1020
Ala Gln Met Glu Pro Gly Ser Ala Val Gly Ala Leu Cys Ala Gln Ser
1025                1030                1035                1040
Ile Gly Glu Pro Gly Thr Gln Met Thr Leu Lys Thr Phe His Phe Gly
                1045                1050                1055
Gly Val Ala Ser Met Asn Ile Thr Leu Gly Val Pro Arg Ile Lys Glu
                1060                1065                1070
Ile Ile Asn Ala Ser Lys Ala Ile Ser Thr Pro Ile Ile Thr Ala Gln
                1075                1080                1085
Leu Asp Lys Asp Asp Ala Asp Tyr Ala Arg Leu Val Lys Gly Arg
    1090                1095                1100
Ile Glu Lys Thr Leu Leu Gly Glu Ile Ser Glu Tyr Ile Glu Glu Val
1105                1110                1115                1120
Phe Leu Pro Asp Asp Cys Phe Ile Leu Val Lys Leu Ser Leu Glu Arg
                1125                1130                1135
Ile Arg Leu Leu Arg Leu Glu Val Asn Ala Glu Thr Val Arg Tyr Ser
    1140                1145                1150
Ile Cys Thr Ser Lys Leu Arg Val Lys Pro Gly Asp Val Ala Val His
    1155                1160                1165
Gly Glu Ala Val Val Cys Val Thr Pro Arg Glu Asn Ser Lys Ser Ser
    1170                1175                1180
Met Tyr Tyr Val Leu Gln Phe Leu Lys Glu Asp Leu Pro Lys Val Val
1185                1190                1195                1200
Val Gln Gly Ile Pro Glu Val Ser Arg Ala Val Ile His Ile Asp Glu
                1205                1210                1215
Gln Ser Gly Lys Glu Lys Tyr Lys Leu Leu Val Glu Gly Asp Asn Leu
                1220                1225                1230
Arg Ala Val Met Ala Thr His Gly Val Lys Gly Thr Arg Thr Thr Ser
                1235                1240                1245
```

```
Asn Asn Thr Tyr Glu Val Glu Lys Thr Leu Gly Ile Glu Ala Ala Arg
    1250                1255                1260

Thr Thr Ile Ile Asn Glu Ile Gln Tyr Thr Met Val Val Asn His Gly
1265                1270                1275                1280

Met Ser Ile Asp Arg Arg His Val Met Leu Leu Ser Asp Leu Met Thr
                1285                1290                1295

Tyr Lys Gly Glu Val Leu Gly Ile Thr Arg Phe Gly Leu Ala Lys Met
            1300                1305                1310

Lys Glu Ser Val Leu Met Leu Ala Ser Phe Glu Lys Thr Ala Asp His
        1315                1320                1325

Leu Phe Asp Ala Ala Tyr Phe Gly Gln Lys Asp Ser Val Cys Gly Val
    1330                1335                1340

Ser Glu Cys Ile Ile Met Gly Ile Pro Met Asn Ile Gly Thr Gly Leu
1345                1350                1355                1360

Phe Lys Leu Leu His Lys Ala Asp Arg Asp Pro Asn Pro Lys Arg
                1365                1370                1375

Pro Leu Ile Phe Asp Thr Asn Glu Phe His Ile Pro Leu Val Thr
            1380                1385                1390

<210> SEQ ID NO 7
<211> LENGTH: 1122
<212> TYPE: DNA
<213> ORGANISM: Homo sapiens
<220> FEATURE:
<221> NAME/KEY: CDS
<222> LOCATION: (1)..(1122)

<400> SEQUENCE: 7 atg gtg aag gag cag ttc cgg gag acg gat gtg gcc aag aaa ata agc      48
Met Val Lys Glu Gln Phe Arg Glu Thr Asp Val Ala Lys Lys Ile Ser
  1               5                  10                  15 cac atc tgt ttt gga atg aag tca cct gag gag atg cgc cag cag gcg      96
His Ile Cys Phe Gly Met Lys Ser Pro Glu Glu Met Arg Gln Gln Ala
             20                  25                  30 cac atc caa gtt gtg agt aag aac ctg tac agc cag gac aac caa cat     144
His Ile Gln Val Val Ser Lys Asn Leu Tyr Ser Gln Asp Asn Gln His
         35                  40                  45 gcc ccc ttg cta tat ggg gtg ctc gac cat agg atg ggt acg agt gag     192
Ala Pro Leu Leu Tyr Gly Val Leu Asp His Arg Met Gly Thr Ser Glu
     50                  55                  60 aag gat cgt cca tgt gaa acc tgt ggg aaa aac ttg gct gac tgt cta     240
Lys Asp Arg Pro Cys Glu Thr Cys Gly Lys Asn Leu Ala Asp Cys Leu
 65                  70                  75                  80 ggc cac tat ggg tat atc gac ctg gag ttg ccg tgt ttt cat gta ggg     288
Gly His Tyr Gly Tyr Ile Asp Leu Glu Leu Pro Cys Phe His Val Gly
                 85                  90                  95 tac ttc aga gca gtc ata ggc atc tta cag atg atc tgc aaa acc tgc     336
Tyr Phe Arg Ala Val Ile Gly Ile Leu Gln Met Ile Cys Lys Thr Cys
            100                 105                 110 tgc cac atc atg ctg tcc caa gag gag aag aag cag ttt ctg gac tat     384
Cys His Ile Met Leu Ser Gln Glu Glu Lys Lys Gln Phe Leu Asp Tyr
        115                 120                 125 cta aag agg ccc ggc ctg acc tac ctt cag aag cga gga ctg aaa aag     432
Leu Lys Arg Pro Gly Leu Thr Tyr Leu Gln Lys Arg Gly Leu Lys Lys
    130                 135                 140 aaa atc tct gac aag tgc cgg aag aaa aac atc tgc cat cac tgt ggc     480
Lys Ile Ser Asp Lys Cys Arg Lys Lys Asn Ile Cys His His Cys Gly
145                 150                 155                 160
```

```
gct ttt aat ggt acc gta aag aag tgt gga ctg ctg aaa ata att cat    528
Ala Phe Asn Gly Thr Val Lys Lys Cys Gly Leu Leu Lys Ile Ile His
                165                 170                 175 gag aaa tac aag acc aac aaa aaa gtg gtg gat ccc att gta tca aat    576
Glu Lys Tyr Lys Thr Asn Lys Lys Val Val Asp Pro Ile Val Ser Asn
            180                 185                 190 ttc ctt cag tct ttt gaa aca gcc att gaa cat aat aaa gaa gtg gag    624
Phe Leu Gln Ser Phe Glu Thr Ala Ile Glu His Asn Lys Glu Val Glu
        195                 200                 205 cct ctg ctg gga agg gca cag gaa aac ttg aat ccc tta gta gtt ctg    672
Pro Leu Leu Gly Arg Ala Gln Glu Asn Leu Asn Pro Leu Val Val Leu
    210                 215                 220 aat tta ttt aaa cga atc cca gct gaa gat gtt cct cta ctt ctg atg    720
Asn Leu Phe Lys Arg Ile Pro Ala Glu Asp Val Pro Leu Leu Leu Met
225                 230                 235                 240 aac cca gaa gcc gga aag ccg tct gat ttg att ctc aca cga ctt ttg    768
Asn Pro Glu Ala Gly Lys Pro Ser Asp Leu Ile Leu Thr Arg Leu Leu
                245                 250                 255 gtg cct cct ttg tgt atc aga ccc tcc gtt gtg agt gat ttg aag tct    816
Val Pro Pro Leu Cys Ile Arg Pro Ser Val Val Ser Asp Leu Lys Ser
            260                 265                 270 ggc acc aat gaa gat gat ctg aca atg aaa ccg aca gaa att att ttc    864
Gly Thr Asn Glu Asp Asp Leu Thr Met Lys Pro Thr Glu Ile Ile Phe
        275                 280                 285 cta aac gat gtt att aaa aag cat cgg atc tca gga gcc aag acc cag    912
Leu Asn Asp Val Ile Lys Lys His Arg Ile Ser Gly Ala Lys Thr Gln
    290                 295                 300 atg atc atg gag gac tgg gat ttc ctg cag ctg cag tgt gcc ctc tac    960
Met Ile Met Glu Asp Trp Asp Phe Leu Gln Leu Gln Cys Ala Leu Tyr
305                 310                 315                 320 att aac agt gag ctc tcg ggc att ccc ctc aac atg gca ccc aag aag    1008
Ile Asn Ser Glu Leu Ser Gly Ile Pro Leu Asn Met Ala Pro Lys Lys
                325                 330                 335 tgg acc aga ggc ttc gtc caa cgc ctg aag gga aaa cag ggt cga ttt    1056
Trp Thr Arg Gly Phe Val Gln Arg Leu Lys Gly Lys Gln Gly Arg Phe
            340                 345                 350 aga gga aat ctc tca gga aag aga gtg gat ttt tct ggc aga aca gtc    1104
Arg Gly Asn Leu Ser Gly Lys Arg Val Asp Phe Ser Gly Arg Thr Val
        355                 360                 365 atc tcg ccc gac ccc aac                                            1122
Ile Ser Pro Asp Pro Asn
    370

<210> SEQ ID NO 8
<211> LENGTH: 374
<212> TYPE: PRT
<213> ORGANISM: Homo sapiens

<400> SEQUENCE: 8

Met Val Lys Glu Gln Phe Arg Glu Thr Asp Val Ala Lys Lys Ile Ser
 1               5                  10                  15

His Ile Cys Phe Gly Met Lys Ser Pro Glu Glu Met Arg Gln Gln Ala
            20                  25                  30

His Ile Gln Val Val Ser Lys Asn Leu Tyr Ser Gln Asp Asn Gln His
        35                  40                  45

Ala Pro Leu Leu Tyr Gly Val Leu Asp His Arg Met Gly Thr Ser Glu
    50                  55                  60

Lys Asp Arg Pro Cys Glu Thr Cys Gly Lys Asn Leu Ala Asp Cys Leu
65                  70                  75                  80
```

```
Gly His Tyr Gly Tyr Ile Asp Leu Glu Leu Pro Cys Phe His Val Gly
                    85                  90                  95

Tyr Phe Arg Ala Val Ile Gly Ile Leu Gln Met Ile Cys Lys Thr Cys
                100                 105                 110

Cys His Ile Met Leu Ser Gln Glu Glu Lys Lys Gln Phe Leu Asp Tyr
                115                 120                 125

Leu Lys Arg Pro Gly Leu Thr Tyr Leu Gln Lys Arg Gly Leu Lys Lys
            130                 135                 140

Lys Ile Ser Asp Lys Cys Arg Lys Lys Asn Ile Cys His His Cys Gly
145                 150                 155                 160

Ala Phe Asn Gly Thr Val Lys Lys Cys Gly Leu Leu Lys Ile Ile His
                165                 170                 175

Glu Lys Tyr Lys Thr Asn Lys Lys Val Val Asp Pro Ile Val Ser Asn
                180                 185                 190

Phe Leu Gln Ser Phe Glu Thr Ala Ile Glu His Asn Lys Glu Val Glu
                195                 200                 205

Pro Leu Leu Gly Arg Ala Gln Glu Asn Leu Asn Pro Leu Val Val Leu
            210                 215                 220

Asn Leu Phe Lys Arg Ile Pro Ala Glu Asp Val Pro Leu Leu Leu Met
225                 230                 235                 240

Asn Pro Glu Ala Gly Lys Pro Ser Asp Leu Ile Leu Thr Arg Leu Leu
                245                 250                 255

Val Pro Pro Leu Cys Ile Arg Pro Ser Val Val Ser Asp Leu Lys Ser
                260                 265                 270

Gly Thr Asn Glu Asp Asp Leu Thr Met Lys Pro Thr Glu Ile Ile Phe
            275                 280                 285

Leu Asn Asp Val Ile Lys Lys His Arg Ile Ser Gly Ala Lys Thr Gln
            290                 295                 300

Met Ile Met Glu Asp Trp Asp Phe Leu Gln Leu Gln Cys Ala Leu Tyr
305                 310                 315                 320

Ile Asn Ser Glu Leu Ser Gly Ile Pro Leu Asn Met Ala Pro Lys Lys
                325                 330                 335

Trp Thr Arg Gly Phe Val Gln Arg Leu Lys Gly Lys Gln Gly Arg Phe
                340                 345                 350

Arg Gly Asn Leu Ser Gly Lys Arg Val Asp Phe Ser Gly Arg Thr Val
            355                 360                 365

Ile Ser Pro Asp Pro Asn
    370

<210> SEQ ID NO 9
<211> LENGTH: 87
<212> TYPE: DNA
<213> ORGANISM: Homo sapiens
<220> FEATURE:
<221> NAME/KEY: CDS
<222> LOCATION: (1)..(87)

<400> SEQUENCE: 9 ggc aga aca gtc atc tcg ccc gac ccc aac ctc cgg att gat gag gta    48
Gly Arg Thr Val Ile Ser Pro Asp Pro Asn Leu Arg Ile Asp Glu Val
 1               5                  10                  15 gct gtg cca gtt cat gtg gcc aaa att cta act ttt cct                 87
Ala Val Pro Val His Val Ala Lys Ile Leu Thr Phe Pro
                20                  25

<210> SEQ ID NO 10
```

```
<211> LENGTH: 29
<212> TYPE: PRT
<213> ORGANISM: Homo sapiens

<400> SEQUENCE: 10

Gly Arg Thr Val Ile Ser Pro Asp Pro Asn Leu Arg Ile Asp Glu Val
 1               5                  10                  15

Ala Val Pro Val His Val Ala Lys Ile Leu Thr Phe Pro
            20                  25

<210> SEQ ID NO 11
<211> LENGTH: 1305
<212> TYPE: DNA
<213> ORGANISM: Homo sapiens
<220> FEATURE:
<221> NAME/KEY: CDS
<222> LOCATION: (1)..(1305)

<400> SEQUENCE: 11
```

| | | | | | | | | | | | | | | | | |
|---|---|---|---|---|---|---|---|---|---|---|---|---|---|---|---|---|
| aac | acg | ggc | aag | ctg | cag | cag | cag | cct | ggc | tgc | act | gct | gag | gag | acc | 48 |
| Asn | Thr | Gly | Lys | Leu | Gln | Gln | Gln | Pro | Gly | Cys | Thr | Ala | Glu | Glu | Thr | |
| 1 | | | | 5 | | | | | 10 | | | | | 15 | | |
| ctg | gag | gca | ctg | atc | ctg | aag | gag | ctg | tct | gtg | atc | cgt | gac | cat | gct | 96 |
| Leu | Glu | Ala | Leu | Ile | Leu | Lys | Glu | Leu | Ser | Val | Ile | Arg | Asp | His | Ala | |
| | | | 20 | | | | | 25 | | | | | 30 | | | |
| ggc | agt | gcc | tgc | ctc | cgg | gag | ctg | gac | aag | agc | aac | agc | ccc | ctc | acc | 144 |
| Gly | Ser | Ala | Cys | Leu | Arg | Glu | Leu | Asp | Lys | Ser | Asn | Ser | Pro | Leu | Thr | |
| | 35 | | | | | 40 | | | | | 45 | | | | | |
| atg | gct | ctg | tgc | ggc | tcc | aaa | ggt | tcc | ttc | att | aac | ata | tca | cag | atg | 192 |
| Met | Ala | Leu | Cys | Gly | Ser | Lys | Gly | Ser | Phe | Ile | Asn | Ile | Ser | Gln | Met | |
| 50 | | | | | 55 | | | | | 60 | | | | | | |
| att | gcc | tgc | gtg | gga | cag | cag | gcc | atc | agt | ggc | tct | cga | gtg | cca | gac | 240 |
| Ile | Ala | Cys | Val | Gly | Gln | Gln | Ala | Ile | Ser | Gly | Ser | Arg | Val | Pro | Asp | |
| 65 | | | | | 70 | | | | | 75 | | | | | 80 | |
| ggc | ttt | gaa | aac | agg | tcc | ttg | cct | cat | ttt | gaa | aaa | cac | tca | aag | ctc | 288 |
| Gly | Phe | Glu | Asn | Arg | Ser | Leu | Pro | His | Phe | Glu | Lys | His | Ser | Lys | Leu | |
| | | | | 85 | | | | | 90 | | | | | 95 | | |
| cca | gct | gcc | aaa | ggc | ttt | gtg | gct | aat | agc | ttt | tat | tcc | ggt | ttg | aca | 336 |
| Pro | Ala | Ala | Lys | Gly | Phe | Val | Ala | Asn | Ser | Phe | Tyr | Ser | Gly | Leu | Thr | |
| | | | 100 | | | | | 105 | | | | | 110 | | | |
| cca | act | gag | ttt | ttc | ttc | cac | aca | atg | gcc | ggc | cgg | gaa | ggt | cta | gtc | 384 |
| Pro | Thr | Glu | Phe | Phe | Phe | His | Thr | Met | Ala | Gly | Arg | Glu | Gly | Leu | Val | |
| | | 115 | | | | | 120 | | | | | 125 | | | | |
| gac | acg | gct | gta | aag | aca | gct | gaa | acg | gga | tac | atg | cag | cga | agg | ctt | 432 |
| Asp | Thr | Ala | Val | Lys | Thr | Ala | Glu | Thr | Gly | Tyr | Met | Gln | Arg | Arg | Leu | |
| | 130 | | | | | 135 | | | | | 140 | | | | | |
| gtc | aaa | tct | ctt | gaa | gat | ctt | tgc | tcc | cag | tat | gat | ctg | aca | gtc | cga | 480 |
| Val | Lys | Ser | Leu | Glu | Asp | Leu | Cys | Ser | Gln | Tyr | Asp | Leu | Thr | Val | Arg | |
| 145 | | | | | 150 | | | | | 155 | | | | | 160 | |
| agc | tct | act | ggc | gat | att | atc | cag | ttc | att | tat | gga | gga | gat | ggc | tta | 528 |
| Ser | Ser | Thr | Gly | Asp | Ile | Ile | Gln | Phe | Ile | Tyr | Gly | Gly | Asp | Gly | Leu | |
| | | | | 165 | | | | | 170 | | | | | 175 | | |
| gat | cct | gca | gct | atg | gag | gga | aaa | gat | gaa | cct | ttg | gag | ttt | aaa | agg | 576 |
| Asp | Pro | Ala | Ala | Met | Glu | Gly | Lys | Asp | Glu | Pro | Leu | Glu | Phe | Lys | Arg | |
| | | | 180 | | | | | 185 | | | | | 190 | | | |
| gtt | ctg | gac | aac | atc | aaa | gca | gtc | ttc | ccg | tgt | ccc | agt | gag | cct | gct | 624 |
| Val | Leu | Asp | Asn | Ile | Lys | Ala | Val | Phe | Pro | Cys | Pro | Ser | Glu | Pro | Ala | |
| | | 195 | | | | | 200 | | | | | 205 | | | | |
| ctc | agc | aaa | aac | gag | ctg | atc | ctg | acc | aca | gag | tcc | atc | atg | aag | aag | 672 |
| Leu | Ser | Lys | Asn | Glu | Leu | Ile | Leu | Thr | Thr | Glu | Ser | Ile | Met | Lys | Lys | |
| | 210 | | | | | 215 | | | | | 220 | | | | | |

```
agt gag ttc ctc tgc tgc cag gac agc ttc ctg cag gaa ata aaa aaa      720
Ser Glu Phe Leu Cys Cys Gln Asp Ser Phe Leu Gln Glu Ile Lys Lys
225                 230                 235                 240 ttc att aag ggg gtc tct gag aag atc aag aaa acc aga gat aaa tat      768
Phe Ile Lys Gly Val Ser Glu Lys Ile Lys Lys Thr Arg Asp Lys Tyr
                245                 250                 255 ggc atc aat gat aac ggc aca aca gag ccc cgt gtg ctg tac cag ctg      816
Gly Ile Asn Asp Asn Gly Thr Thr Glu Pro Arg Val Leu Tyr Gln Leu
            260                 265                 270 gac cgc atc acc ccc acc caa gta gaa aag ttt ctg gag acc tgt agg      864
Asp Arg Ile Thr Pro Thr Gln Val Glu Lys Phe Leu Glu Thr Cys Arg
        275                 280                 285 gac aag tac atg agg gca cag atg gag cct ggt tct gca gtg ggt gct      912
Asp Lys Tyr Met Arg Ala Gln Met Glu Pro Gly Ser Ala Val Gly Ala
    290                 295                 300 ctg tgt gcc cag agc att ggt gag cca ggc acc cag atg acc ctg aag      960
Leu Cys Ala Gln Ser Ile Gly Glu Pro Gly Thr Gln Met Thr Leu Lys
305                 310                 315                 320 act ttc cac ttt gca ggt gtg gcc tcc atg aac atc acc ctg ggc gtg     1008
Thr Phe His Phe Ala Gly Val Ala Ser Met Asn Ile Thr Leu Gly Val
                325                 330                 335 ccc cgg att aaa gag atc atc aac gct tcc aag gcc atc agc act cca     1056
Pro Arg Ile Lys Glu Ile Ile Asn Ala Ser Lys Ala Ile Ser Thr Pro
            340                 345                 350 att atc aca gca cag cta gac aag gat gac gac gcg gat tat gct cgc     1104
Ile Ile Thr Ala Gln Leu Asp Lys Asp Asp Asp Ala Asp Tyr Ala Arg
        355                 360                 365 ctc gtg aaa ggg aga att gag aaa acc ctc ttg gga gag att tcc gag     1152
Leu Val Lys Gly Arg Ile Glu Lys Thr Leu Leu Gly Glu Ile Ser Glu
    370                 375                 380 tat att gaa gaa gtg ttt ctt cct gat gac tgc ttt att ctc gtc aag     1200
Tyr Ile Glu Glu Val Phe Leu Pro Asp Asp Cys Phe Ile Leu Val Lys
385                 390                 395                 400 ctc tcc ctg gaa cgg att agg ctt ctg aga ctg gaa gtg aac gct gag     1248
Leu Ser Leu Glu Arg Ile Arg Leu Leu Arg Leu Glu Val Asn Ala Glu
                405                 410                 415 aca gtg aga tat tcc atc tgc aca tcc aag ctc cgt gtg aag ccc ggt     1296
Thr Val Arg Tyr Ser Ile Cys Thr Ser Lys Leu Arg Val Lys Pro Gly
            420                 425                 430 gat gtg gct                                                         1305
Asp Val Ala
        435

<210> SEQ ID NO 12
<211> LENGTH: 435
<212> TYPE: PRT
<213> ORGANISM: Homo sapiens

<400> SEQUENCE: 12

Asn Thr Gly Lys Leu Gln Gln Gln Pro Gly Cys Thr Ala Glu Glu Thr
 1               5                  10                  15

Leu Glu Ala Leu Ile Leu Lys Glu Leu Ser Val Ile Arg Asp His Ala
            20                  25                  30

Gly Ser Ala Cys Leu Arg Glu Leu Asp Lys Ser Asn Ser Pro Leu Thr
        35                  40                  45

Met Ala Leu Cys Gly Ser Lys Gly Ser Phe Ile Asn Ile Ser Gln Met
    50                  55                  60

Ile Ala Cys Val Gly Gln Gln Ala Ile Ser Gly Ser Arg Val Pro Asp
65                  70                  75                  80
```

-continued

```
Gly Phe Glu Asn Arg Ser Leu Pro His Phe Glu Lys His Ser Lys Leu
                 85                  90                  95

Pro Ala Ala Lys Gly Phe Val Ala Asn Ser Phe Tyr Ser Gly Leu Thr
            100                 105                 110

Pro Thr Glu Phe Phe His Thr Met Ala Gly Arg Glu Gly Leu Val
        115                 120                 125

Asp Thr Ala Val Lys Thr Ala Glu Thr Gly Tyr Met Gln Arg Arg Leu
130                 135                 140

Val Lys Ser Leu Glu Asp Leu Cys Ser Gln Tyr Asp Leu Thr Val Arg
145                 150                 155                 160

Ser Ser Thr Gly Asp Ile Ile Gln Phe Ile Tyr Gly Gly Asp Gly Leu
                165                 170                 175

Asp Pro Ala Ala Met Glu Gly Lys Asp Glu Pro Leu Glu Phe Lys Arg
            180                 185                 190

Val Leu Asp Asn Ile Lys Ala Val Phe Pro Cys Pro Ser Glu Pro Ala
        195                 200                 205

Leu Ser Lys Asn Glu Leu Ile Leu Thr Thr Glu Ser Ile Met Lys Lys
210                 215                 220

Ser Glu Phe Leu Cys Cys Gln Asp Ser Phe Leu Gln Glu Ile Lys Lys
225                 230                 235                 240

Phe Ile Lys Gly Val Ser Glu Lys Ile Lys Lys Thr Arg Asp Lys Tyr
                245                 250                 255

Gly Ile Asn Asp Asn Gly Thr Thr Glu Pro Arg Val Leu Tyr Gln Leu
            260                 265                 270

Asp Arg Ile Thr Pro Thr Gln Val Glu Lys Phe Leu Glu Thr Cys Arg
        275                 280                 285

Asp Lys Tyr Met Arg Ala Gln Met Glu Pro Gly Ser Ala Val Gly Ala
290                 295                 300

Leu Cys Ala Gln Ser Ile Gly Glu Pro Gly Thr Gln Met Thr Leu Lys
305                 310                 315                 320

Thr Phe His Phe Ala Gly Val Ala Ser Met Asn Ile Thr Leu Gly Val
                325                 330                 335

Pro Arg Ile Lys Glu Ile Ile Asn Ala Ser Lys Ala Ile Ser Thr Pro
            340                 345                 350

Ile Ile Thr Ala Gln Leu Asp Lys Asp Asp Ala Asp Tyr Ala Arg
        355                 360                 365

Leu Val Lys Gly Arg Ile Glu Lys Thr Leu Leu Gly Glu Ile Ser Glu
370                 375                 380

Tyr Ile Glu Glu Val Phe Leu Pro Asp Asp Cys Phe Ile Leu Val Lys
385                 390                 395                 400

Leu Ser Leu Glu Arg Ile Arg Leu Leu Arg Leu Glu Val Asn Ala Glu
                405                 410                 415

Thr Val Arg Tyr Ser Ile Cys Thr Ser Lys Leu Arg Val Lys Pro Gly
            420                 425                 430

Asp Val Ala
        435
```

<210> SEQ ID NO 13
<211> LENGTH: 900
<212> TYPE: DNA
<213> ORGANISM: Homo sapiens
<220> FEATURE:
<221> NAME/KEY: CDS
<222> LOCATION: (1)..(900)

<400> SEQUENCE: 13

```
gat gac gac gcg gat tat gct cgc ctc gtg aaa ggg aga att gag aaa     48
Asp Asp Asp Ala Asp Tyr Ala Arg Leu Val Lys Gly Arg Ile Glu Lys
 1               5                  10                  15 acc ctc ttg gga gag att tcc gag tat att gaa gaa gtg ttt ctt cct     96
Thr Leu Leu Gly Glu Ile Ser Glu Tyr Ile Glu Glu Val Phe Leu Pro
             20                  25                  30 gat gac tgc ttt att ctc gtc aag ctc tcc ctg gaa cgg att agg ctt    144
Asp Asp Cys Phe Ile Leu Val Lys Leu Ser Leu Glu Arg Ile Arg Leu
         35                  40                  45 ctg aga ctg gaa gtg aac gct gag aca gtg aga tat tcc atc tgc aca    192
Leu Arg Leu Glu Val Asn Ala Glu Thr Val Arg Tyr Ser Ile Cys Thr
 50                  55                  60 tcc aag ctc cgt gtg aag ccc ggt gat gtg gct gtt cat ggt gag gct    240
Ser Lys Leu Arg Val Lys Pro Gly Asp Val Ala Val His Gly Glu Ala
 65                  70                  75                  80 gtg gtg tgt gtc acc ccc aga gag aac agc aag agc tcc atg tac tac    288
Val Val Cys Val Thr Pro Arg Glu Asn Ser Lys Ser Ser Met Tyr Tyr
                 85                  90                  95 gtg ctg cag ttc ctg aaa gag gat ctc ccc aag gtg gtg gtg cag ggc    336
Val Leu Gln Phe Leu Lys Glu Asp Leu Pro Lys Val Val Val Gln Gly
             100                 105                 110 att cca gag gtg tcc aga gct gtc atc cac att gac gag cag agt gga    384
Ile Pro Glu Val Ser Arg Ala Val Ile His Ile Asp Glu Gln Ser Gly
         115                 120                 125 aag gag aag tac aag ctt ctg gtg gaa ggt gat aac ctg cgg gca gtc    432
Lys Glu Lys Tyr Lys Leu Leu Val Glu Gly Asp Asn Leu Arg Ala Val
130                 135                 140 atg gcc aca cac ggt gtg aag ggc acc cga acc acc tcc aat aac acc    480
Met Ala Thr His Gly Val Lys Gly Thr Arg Thr Thr Ser Asn Asn Thr
145                 150                 155                 160 tat gag gtg gag aaa act ctg ggc atc gag gcc gcc cgg aca acg atc    528
Tyr Glu Val Glu Lys Thr Leu Gly Ile Glu Ala Ala Arg Thr Thr Ile
                 165                 170                 175 atc aat gaa atc cag tac acc atg gtg aac cac ggc atg agc atc gac    576
Ile Asn Glu Ile Gln Tyr Thr Met Val Asn His Gly Met Ser Ile Asp
             180                 185                 190 agg agg cac gtg atg ctg ctc tcc gac ctc atg acc tac aag ggt gaa    624
Arg Arg His Val Met Leu Leu Ser Asp Leu Met Thr Tyr Lys Gly Glu
         195                 200                 205 gtc ctg ggc atc act agg ttt ggc ctg gcc aag atg aag gag agt gtg    672
Val Leu Gly Ile Thr Arg Phe Gly Leu Ala Lys Met Lys Glu Ser Val
210                 215                 220 ctg atg ctg gcc tcc ttt gag aag acg gct gac cat ctc ttt gac gct    720
Leu Met Leu Ala Ser Phe Glu Lys Thr Ala Asp His Leu Phe Asp Ala
225                 230                 235                 240 gcc tac ttc ggg cag aag gac tct gtg tgt ggg gtg tct gag tgc atc    768
Ala Tyr Phe Gly Gln Lys Asp Ser Val Cys Gly Val Ser Glu Cys Ile
                 245                 250                 255 atc atg gga atc cca atg aac att gga acc ggg ctc ttc aag ctg ctt    816
Ile Met Gly Ile Pro Met Asn Ile Gly Thr Gly Leu Phe Lys Leu Leu
             260                 265                 270 cac aag gct gac agg gac ccg aac cct ccc aag agg ccc ctg atc ttc    864
His Lys Ala Asp Arg Asp Pro Asn Pro Pro Lys Arg Pro Leu Ile Phe
         275                 280                 285 gac aca aat gaa ttc cac atc ccc ctt gtc aca tag                    900
Asp Thr Asn Glu Phe His Ile Pro Leu Val Thr
         290                 295                 300
```

<210> SEQ ID NO 14

```
<211> LENGTH: 299
<212> TYPE: PRT
<213> ORGANISM: Homo sapiens

<400> SEQUENCE: 14

Asp Asp Asp Ala Asp Tyr Ala Arg Leu Val Lys Gly Arg Ile Glu Lys
  1               5                  10                  15

Thr Leu Leu Gly Glu Ile Ser Glu Tyr Ile Glu Val Phe Leu Pro
             20                  25                  30

Asp Asp Cys Phe Ile Leu Val Lys Leu Ser Leu Glu Arg Ile Arg Leu
             35                  40                  45

Leu Arg Leu Glu Val Asn Ala Glu Thr Val Arg Tyr Ser Ile Cys Thr
 50                  55                  60

Ser Lys Leu Arg Val Lys Pro Gly Asp Val Ala Val His Gly Glu Ala
 65                  70                  75                  80

Val Val Cys Val Thr Pro Arg Glu Asn Ser Lys Ser Met Tyr Tyr
             85                  90                  95

Val Leu Gln Phe Leu Lys Glu Asp Leu Pro Lys Val Val Gln Gly
            100                 105                 110

Ile Pro Glu Val Ser Arg Ala Val Ile His Ile Asp Glu Gln Ser Gly
            115                 120                 125

Lys Glu Lys Tyr Lys Leu Leu Val Gly Asp Asn Leu Arg Ala Val
130                 135                 140

Met Ala Thr His Gly Val Lys Gly Thr Arg Thr Thr Ser Asn Asn Thr
145                 150                 155                 160

Tyr Glu Val Glu Lys Thr Leu Gly Ile Glu Ala Ala Arg Thr Thr Ile
                165                 170                 175

Ile Asn Glu Ile Gln Tyr Thr Met Val Asn His Gly Met Ser Ile Asp
            180                 185                 190

Arg Arg His Val Met Leu Leu Ser Asp Leu Met Thr Tyr Lys Gly Glu
        195                 200                 205

Val Leu Gly Ile Thr Arg Phe Gly Leu Ala Lys Met Lys Glu Ser Val
    210                 215                 220

Leu Met Leu Ala Ser Phe Glu Lys Thr Ala Asp His Leu Phe Asp Ala
225                 230                 235                 240

Ala Tyr Phe Gly Gln Lys Asp Ser Val Cys Gly Val Ser Glu Cys Ile
                245                 250                 255

Ile Met Gly Ile Pro Met Asn Ile Gly Thr Gly Leu Phe Lys Leu Leu
            260                 265                 270

His Lys Ala Asp Arg Asp Pro Asn Pro Lys Arg Pro Leu Ile Phe
        275                 280                 285

Asp Thr Asn Glu Phe His Ile Pro Leu Val Thr
    290                 295

<210> SEQ ID NO 15
<211> LENGTH: 27
<212> TYPE: DNA
<213> ORGANISM: Artificial Sequence
<220> FEATURE:
<223> OTHER INFORMATION: Description of Artificial Sequence:RPC62 sense
      primer

<400> SEQUENCE: 15
ctcagactcc ccagtacaat gactcaa                                            27

<210> SEQ ID NO 16
<211> LENGTH: 27
```

```
<212> TYPE: DNA
<213> ORGANISM: Artificial Sequence
<220> FEATURE:
<223> OTHER INFORMATION: Description of Artificial Sequence:
      RPC62 antisense
      primer

<400> SEQUENCE: 16
ccaggcacct cctttatttt gctttcc                                          27

<210> SEQ ID NO 17
<211> LENGTH: 22
<212> TYPE: DNA
<213> ORGANISM: Artificial Sequence
<220> FEATURE:
<223> OTHER INFORMATION: Description of Artificial Sequence:RPC155-A
      sense primer

<400> SEQUENCE: 17
atggtgaagg agcagttccg gg                                               22

<210> SEQ ID NO 18
<211> LENGTH: 22
<212> TYPE: DNA
<213> ORGANISM: Artificial Sequence
<220> FEATURE:
<223> OTHER INFORMATION: Description of Artificial Sequence:RPC155-A
      antisence primer

<400> SEQUENCE: 18
aggttggggt cgggcgagat ga                                               22

<210> SEQ ID NO 19
<211> LENGTH: 22
<212> TYPE: DNA
<213> ORGANISM: Artificial Sequence
<220> FEATURE:
<223> OTHER INFORMATION: Description of Artificial Sequence:RPC155-B
      sense primer

<400> SEQUENCE: 19
tggcagaaca gtcatctcgc cc                                               22

<210> SEQ ID NO 20
<211> LENGTH: 22
<212> TYPE: DNA
<213> ORGANISM: Artificial Sequence
<220> FEATURE:
<223> OTHER INFORMATION: Description of Artificial Sequence:RPC155-B
      antisense primer

<400> SEQUENCE: 20
atcagtgcct ccagggtctc ct                                               22

<210> SEQ ID NO 21
<211> LENGTH: 23
<212> TYPE: DNA
<213> ORGANISM: Artificial Sequence
<220> FEATURE:
<223> OTHER INFORMATION: Description of Artificial Sequence:RPC155-C
      sense primer

<400> SEQUENCE: 21
aacacgggca agctgcagca gca                                              23

<210> SEQ ID NO 22
<211> LENGTH: 22
```

```
<212> TYPE: DNA
<213> ORGANISM: Artificial Sequence
<220> FEATURE:
<223> OTHER INFORMATION: Description of Artificial Sequence:RPC155-C
      antisense primer

<400> SEQUENCE: 22
ccatgaacag ccacatcacc gg                                              22

<210> SEQ ID NO 23
<211> LENGTH: 26
<212> TYPE: DNA
<213> ORGANISM: Artificial Sequence
<220> FEATURE:
<223> OTHER INFORMATION: Description of Artificial Sequence:RPC155-D
      sense primer

<400> SEQUENCE: 23
aggatgacga cgcggattat gctcgc                                          26

<210> SEQ ID NO 24
<211> LENGTH: 27
<212> TYPE: DNA
<213> ORGANISM: Artificial Sequence
<220> FEATURE:
<223> OTHER INFORMATION: Description of Artificial Sequence:RPC155-D
      antisense primer

<400> SEQUENCE: 24
ctatgtgaca aggggggatgt ggaattc                                        27

<210> SEQ ID NO 25
<211> LENGTH: 22
<212> TYPE: DNA
<213> ORGANISM: Artificial Sequence
<220> FEATURE:
<223> OTHER INFORMATION: Description of Artificial Sequence:RPC155-C1
      sense primer

<400> SEQUENCE: 25
gggaattcaa cacgggcaag ct                                              22

<210> SEQ ID NO 26
<211> LENGTH: 24
<212> TYPE: DNA
<213> ORGANISM: Artificial Sequence
<220> FEATURE:
<223> OTHER INFORMATION: Description of Artificial Sequence:RPC155-C1
      antisense primer

<400> SEQUENCE: 26
gctctagatc acccatctcc tcca                                            24

<210> SEQ ID NO 27
<211> LENGTH: 22
<212> TYPE: DNA
<213> ORGANISM: Artificial Sequence
<220> FEATURE:
<223> OTHER INFORMATION: Description of Artificial Sequence:RPC155-C2
      sense primer

<400> SEQUENCE: 27
gggaattcaa cacgggcaag ct                                              22

<210> SEQ ID NO 28
<211> LENGTH: 25
<212> TYPE: DNA
```

```
<213> ORGANISM: Artificial Sequence
<220> FEATURE:
<223> OTHER INFORMATION: Description of Artificial Sequence:RPC155-C2
      antisense primer

<400> SEQUENCE: 28
ggtctagatc agggcaggaa gctgt                                          25

<210> SEQ ID NO 29
<211> LENGTH: 22
<212> TYPE: DNA
<213> ORGANISM: Artificial Sequence
<220> FEATURE:
<223> OTHER INFORMATION: Description of Artificial Sequence:RPC155-C3
      sense primer

<400> SEQUENCE: 29
gggaattcaa cacgggcaag ct                                             22

<210> SEQ ID NO 30
<211> LENGTH: 23
<212> TYPE: DNA
<213> ORGANISM: Artificial Sequence
<220> FEATURE:
<223> OTHER INFORMATION: Description of Artificial Sequence:RPC155-C3
      antisense primer

<400> SEQUENCE: 30
cgtctagatc agatggcctt gga                                            23

<210> SEQ ID NO 31
<211> LENGTH: 23
<212> TYPE: DNA
<213> ORGANISM: Artificial Sequence
<220> FEATURE:
<223> OTHER INFORMATION: Description of Artificial Sequence:RPC155-C4
      sense primer

<400> SEQUENCE: 31
ccgaattccg aagctctact ggc                                            23

<210> SEQ ID NO 32
<211> LENGTH: 24
<212> TYPE: DNA
<213> ORGANISM: Artificial Sequence
<220> FEATURE:
<223> OTHER INFORMATION: Description of Artificial Sequence:RPC155-C4
      antisense primer

<400> SEQUENCE: 32
ggtctagatc acagccacat cacc                                           24

<210> SEQ ID NO 33
<211> LENGTH: 23
<212> TYPE: DNA
<213> ORGANISM: Artificial Sequence
<220> FEATURE:
<223> OTHER INFORMATION: Description of Artificial Sequence:RPC155-C5
      sense primer

<400> SEQUENCE: 33
ttgaattcga ccgcatcacc ccc                                            23

<210> SEQ ID NO 34
<211> LENGTH: 24
<212> TYPE: DNA
<213> ORGANISM: Artificial Sequence
```

```
<220> FEATURE:
<223> OTHER INFORMATION: Description of Artificial Sequence:RPC155-C5
      antisense primer

<400> SEQUENCE: 34
ggtctagatc acagccacat cacc                                              24

<210> SEQ ID NO 35
<211> LENGTH: 23
<212> TYPE: DNA
<213> ORGANISM: Artificial Sequence
<220> FEATURE:
<223> OTHER INFORMATION: Description of Artificial Sequence:RPC155-C-a
      sense primer

<400> SEQUENCE: 35
ccgaattccg aagctctact ggc                                               23

<210> SEQ ID NO 36
<211> LENGTH: 25
<212> TYPE: DNA
<213> ORGANISM: Artificial Sequence
<220> FEATURE:
<223> OTHER INFORMATION: Description of Artificial Sequence:RPC155-C-a
      antisense primer

<400> SEQUENCE: 36
ggtctagatc agggcaggaa gctgt                                             25

<210> SEQ ID NO 37
<211> LENGTH: 23
<212> TYPE: DNA
<213> ORGANISM: Artificial Sequence
<220> FEATURE:
<223> OTHER INFORMATION: Description of Artificial Sequence:RPC155-C-b
      sense primer

<400> SEQUENCE: 37
ccgaattccg aagctctact ggc                                               23

<210> SEQ ID NO 38
<211> LENGTH: 23
<212> TYPE: DNA
<213> ORGANISM: Artificial Sequence
<220> FEATURE:
<223> OTHER INFORMATION: Description of Artificial Sequence:RPC155-C-b
      antisense primer

<400> SEQUENCE: 38
actctagatc aggtgatgcg gtc                                               23

<210> SEQ ID NO 39
<211> LENGTH: 23
<212> TYPE: DNA
<213> ORGANISM: Artificial Sequence
<220> FEATURE:
<223> OTHER INFORMATION: Description of Artificial Sequence:RPC155-C-c
      sense primer

<400> SEQUENCE: 39
ccgaattccg aagctctact ggc                                               23

<210> SEQ ID NO 40
<211> LENGTH: 23
<212> TYPE: DNA
<213> ORGANISM: Artificial Sequence
<220> FEATURE:
```

```
<223> OTHER INFORMATION: Description of Artificial Sequence:RPC155-C-c
      antisense primer

<400> SEQUENCE: 40
gctctagatc agtccctaca ggt                                           23

<210> SEQ ID NO 41
<211> LENGTH: 23
<212> TYPE: DNA
<213> ORGANISM: Artificial Sequence
<220> FEATURE:
<223> OTHER INFORMATION: Description of Artificial Sequence:RPC155-C-d
      sense primer

<400> SEQUENCE: 41
gggaattcga gtccatcatg aag                                           23

<210> SEQ ID NO 42
<211> LENGTH: 23
<212> TYPE: DNA
<213> ORGANISM: Artificial Sequence
<220> FEATURE:
<223> OTHER INFORMATION: Description of Artificial Sequence:RPC155-C-d
      antisense primer

<400> SEQUENCE: 42
cgtctagatc agatggcctt gga                                           23

<210> SEQ ID NO 43
<211> LENGTH: 22
<212> TYPE: DNA
<213> ORGANISM: Artificial Sequence
<220> FEATURE:
<223> OTHER INFORMATION: Description of Artificial Sequence:RPC155-C-e
      sense primer

<400> SEQUENCE: 43
gcgaattcca ggacagcttc ct                                            22

<210> SEQ ID NO 44
<211> LENGTH: 23
<212> TYPE: DNA
<213> ORGANISM: Artificial Sequence
<220> FEATURE:
<223> OTHER INFORMATION: Description of Artificial Sequence:RPC-C-e
      antisense primer

<400> SEQUENCE: 44
cgtctagatc agatggcctt gga                                           23

<210> SEQ ID NO 45
<211> LENGTH: 23
<212> TYPE: DNA
<213> ORGANISM: Artificial Sequence
<220> FEATURE:
<223> OTHER INFORMATION: Description of Artificial Sequence:RPC-C-f
      sense primer

<400> SEQUENCE: 45
ttgaattcga ccgcatcacc ccc                                           23

<210> SEQ ID NO 46
<211> LENGTH: 23
<212> TYPE: DNA
<213> ORGANISM: Artificial Sequence
<220> FEATURE:
<223> OTHER INFORMATION: Description of Artificial Sequence:RPC-C-f
```

-continued

```
antisense primer

<400> SEQUENCE: 46
cgtctagatc agatggcctt gga                                                23

<210> SEQ ID NO 47
<211> LENGTH: 23
<212> TYPE: DNA
<213> ORGANISM: Artificial Sequence
<220> FEATURE:
<223> OTHER INFORMATION: Description of Artificial Sequence:RPC-C-g
      sense primer

<400> SEQUENCE: 47
ccgaattccg aagctctact ggc                                                23

<210> SEQ ID NO 48
<211> LENGTH: 23
<212> TYPE: DNA
<213> ORGANISM: Artificial Sequence
<220> FEATURE:
<223> OTHER INFORMATION: Description of Artificial Sequence:RPC155-C-C-g
      antisense primer

<400> SEQUENCE: 48
cgtctagatc agatggcctt gga                                                23
```